United States Patent
Mizunaka et al.

(10) Patent No.: US 12,329,495 B2
(45) Date of Patent: Jun. 17, 2025

(54) ENDOSCOPE SYSTEM

(71) Applicant: OLYMPUS CORPORATION, Tokyo (JP)

(72) Inventors: Masaru Mizunaka, Hino (JP); Yasunobu Iga, Tachikawa (JP); Takeshi Suga, Hino (JP); Chikashi Ota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 305 days.

(21) Appl. No.: 17/971,819

(22) Filed: Oct. 24, 2022

(65) Prior Publication Data
US 2023/0371817 A1 Nov. 23, 2023

Related U.S. Application Data

(60) Provisional application No. 63/344,744, filed on May 23, 2022.

(51) Int. Cl.
*A61B 5/00* (2006.01)
*A61B 1/00* (2006.01)
(Continued)

(52) U.S. Cl.
CPC .......... *A61B 5/0071* (2013.01); *A61B 1/0005* (2013.01); *A61B 1/045* (2013.01);
(Continued)

(58) Field of Classification Search
CPC .............. A61B 1/00006; A61B 1/0005; A61B 1/00186; A61B 1/043; A61B 1/045;
(Continued)

(56) References Cited

U.S. PATENT DOCUMENTS

| | | | | |
|---|---|---|---|---|
| 5,241,170 A | * | 8/1993 | Field, Jr. .............. | A61B 1/0646 606/15 |
| 2003/0120129 A1 | * | 6/2003 | Nakamura ........... | A61B 1/0676 600/101 |

(Continued)

FOREIGN PATENT DOCUMENTS

| | | |
|---|---|---|
| WO | 2019/215796 A1 | 11/2019 |
| WO | WO-2020075247 A1 * | 4/2020 |

OTHER PUBLICATIONS

English translation of Sato et al. (WO 2020/075247) (Year: 2020).*

*Primary Examiner* — Katherine L Fernandez
(74) *Attorney, Agent, or Firm* — Scully, Scott, Murphy & Presser, P.C.

(57) ABSTRACT

An endoscope system according to the present invention includes: an illumination light source that emits illumination light for illuminating an object; a therapeutic light source that emits therapeutic light for causing a photoreactive reagent accumulated in a treatment target site to react; a guide light source that emits guide light having a wavelength shorter than a wavelength band of the therapeutic light source; an imager that captures an optical image, the imager including an optical filter that cuts light in the wavelength band of the therapeutic light and transmits a part of white light, the guide light, and fluorescence emitted by the reagent; a controller that controls emission timings of the illumination light source, the therapeutic light source, and the guide light source; and an image processor that generates an image on the basis of an optical image obtained by light emitted from the illumination light source, the therapeutic light source, and the guide light source, in which the controller causes the image processor to generate an illumination light image based on an optical image acquired during a period in which the illumination light source and the guide light source are ON and to generate a fluorescence
(Continued)

image based on a fluorescence image acquired during a period in which the therapeutic light source is ON and the illumination light source and the guide light source are OFF.

20 Claims, 13 Drawing Sheets

(51) Int. Cl.
*A61B 1/045* (2006.01)
*A61B 1/06* (2006.01)
*A61N 5/06* (2006.01)

(52) U.S. Cl.
CPC .......... *A61B 1/0646* (2013.01); *A61B 1/0655* (2022.02); *A61N 5/0603* (2013.01); *A61N 5/062* (2013.01)

(58) Field of Classification Search
CPC ... A61B 1/0638; A61B 1/0646; A61B 1/0655; A61B 1/07; A61B 5/0071; A61B 5/0084; A61N 2005/0626; A61N 2005/0659; A61N 5/0603; A61N 5/062
See application file for complete search history.

(56) References Cited

U.S. PATENT DOCUMENTS

2005/0288556 A1\* 12/2005 Sugimoto ............ A61B 1/0646
600/178
2017/0032521 A1\* 2/2017 Kubo ................. A61B 1/00009

\* cited by examiner

ENDOSCOPE SYSTEM

TECHNICAL FIELD

The present invention relates to an endoscope system.

BACKGROUND ART

In recent years, research has been advanced on photoimmunotherapy (PIT) for treating cancer by causing an antibody drug to be specifically bound to protein of cancer cells and activating the antibody drug by irradiation with near-infrared light, which is therapeutic light, and thereby destroying the cancer cells. The antibody drug irradiated with near-infrared light expands the cancer cells and induces cell death of the cancer cells. At this point, the antibody drug emits fluorescence by being excited.

Meanwhile, white light is used for observation of a treatment site, and fluorescence observation using excitation light can be used for observation of the binding of the antibody drug to the tissue or the therapeutic effects. At this point, in a case where one sheet of imaging element is used in an observation optical system, fluorescence observation can be performed by the observation optical system using a filter that cuts off excitation light.

In order to appropriately perform PIT treatment also at the time of fluorescence observation, it is important to observe the treatment site and to grasp the irradiation area of the near-infrared light, however, since the fluorescence is weaker as compared to the intensity of white light, it is difficult to perform both the observation of the treatment site with white light and the fluorescence observation. In addition, since the excitation light is cut by the filter, it is also difficult to observe the irradiation area of the excitation light (for example, near-infrared light). As a countermeasure against this, it is conceivable to emit, as guide light, light in a wavelength band that is not cut by the filter to substantially the same region as the region where the near-infrared light is emitted to, however, if the fluorescence is weak with respect to the light intensity of the guide light, it is difficult to observe the fluorescence.

Meanwhile, as technology for processing white light or fluorescence, there is known technology for processing observation light in each observation by separating fluorescence and other light by a beam splitter and providing a plurality of imaging elements for receiving each ray of light (see, for example, Patent Literature 1). With the configuration of two sheets of imaging elements disclosed in Patent Literature 1, the treatment site can be continuously observed at the time of fluorescence observation.

CITATION LIST

Patent Literature

Patent Literature 1: WO 2019/215796 A

DISCLOSURE OF INVENTION

Problem to be Solved by the Invention

However, the configuration including the two plates of imaging elements as in Patent Literature 1 increases the number of components of an imaging optical system, thereby leading to an increase in the size of the device. In a device including an optical system at a portion to be inserted into a subject like an endoscope, this configuration cannot be adopted since the diameter of an insertion unit is increased.

The present invention has been made in view of the above, and an object of the invention is to provide an endoscope system capable of continuously observing a treatment site at the time of fluorescence observation while preventing an increase in the diameter.

Means for Solving Problem

To solve the problem described above and to achieve the object, an endoscope system according to the present invention includes: an illumination light source configured to emit illumination light for illuminating an object; a therapeutic light source configured to emit therapeutic light for causing a photoreactive reagent accumulated in a treatment target site to react; a guide light source configured to emit guide light having a wavelength shorter than a wavelength band of the therapeutic light source; an imager configured to capture an optical image, the imager including an optical filter configured to cut light in the wavelength band of the therapeutic light and transmit a part of white light, the guide light, and fluorescence emitted by the reagent; a controller configured to control emission timings of the illumination light source, the therapeutic light source, and the guide light source; and an image processor configured to generate an image based on an optical image obtained by light emitted from the illumination light source, the therapeutic light source, and the guide light source. The controller is configured to cause the image processor to generate an illumination light image based on an optical image acquired during a period in which the illumination light source and the guide light source are ON and to generate a fluorescence image based on a fluorescence image acquired during a period in which the therapeutic light source is ON and the illumination light source and the guide light source are OFF.

In the endoscope system according to the present invention, the image processor is configured to generate the illumination light image based on an optical image by emission of the illumination light and the guide light and a superimposed image in which the fluorescence image based on an optical image by the fluorescence is superimposed on the illumination light image, and the endoscope system further includes: a display configured to display the illumination light image and/or the superimposed image.

In the endoscope system according to the present invention, the controller is configured to control ON and OFF of the illumination light source and the guide light source and imaging timing of the imager in synchronization with each other, and the therapeutic light source is controlled independently of the illumination light source and the guide light source.

In the endoscope system according to the present invention, the controller is configured to control ON and OFF of the illumination light source and the guide light source, ON and OFF of the therapeutic light source, and imaging timing of the imager in synchronization with each other.

In the endoscope system according to the present invention, the illumination light source is subjected to dimming control using a value obtained by subtracting a signal value corresponding to an amount of the guide light which is emitted, from a detected light amount.

In the endoscope system according to the present invention, the illumination light source is subjected to dimming control based on a light amount in a range excluding an irradiation range of the guide light.

In the endoscope system according to the present invention, the illumination light source is configured to emit light in a wavelength band other than a wavelength band of the guide light.

In the endoscope system according to the present invention, the illumination light source is configured to emit light of only both of a blue component and a green component or only the blue component.

In the endoscope system according to the present invention, the controller is configured to cause the image processor to generate an illumination light image based on an optical image acquired during a period in which the illumination light source and the guide light source are ON and the therapeutic light source is OFF and to generate a fluorescence image based on a fluorescence image acquired during a period in which the illumination light source and the guide light source are OFF and the therapeutic light source is ON.

In the endoscope system according to the present invention, the controller is configured to cause the imager to capture a fluorescence image when a signal value of at least one of a blue component and a green component in an optical image acquired during a period in which the illumination light source and the guide light source are OFF is less than or equal to a preset threshold value.

In the endoscope system according to the present invention, the controller is configured to normalize the fluorescence image by using a light intensity or an irradiation diameter of an irradiation area of the guide light in the illumination light image.

In the endoscope system according to the present invention, the controller is configured to correct an amount of the therapeutic light by using a light intensity or an irradiation diameter of an irradiation area of the guide light in the illumination light image.

In the endoscope system according to the present invention, the controller is configured to correct a light intensity of the therapeutic light with a distance using a light intensity or an irradiation diameter of the guide light and calculate a treatment time using the light intensity that has been corrected.

Effect of the Invention

According to the present invention, there is an effect that it is possible to continuously observe a treatment site at the time of fluorescence observation while preventing an increase in the diameter.

MODE(S) OF CARRYING OUT THE INVENTION

Embodiments for carrying out the present invention (hereinafter referred to as "embodiments") will be described below. In the embodiments, as an example of an endoscope system of the present invention, an endoscope device for medical use for performing photoimmunotherapy that captures and displays an in-vivo image of a patient or the like. Note that the present invention is not limited by the embodiments. Moreover, in the description of the drawings, the same part is denoted by the same symbol and thereby described.

First Embodiment

Figure 1:
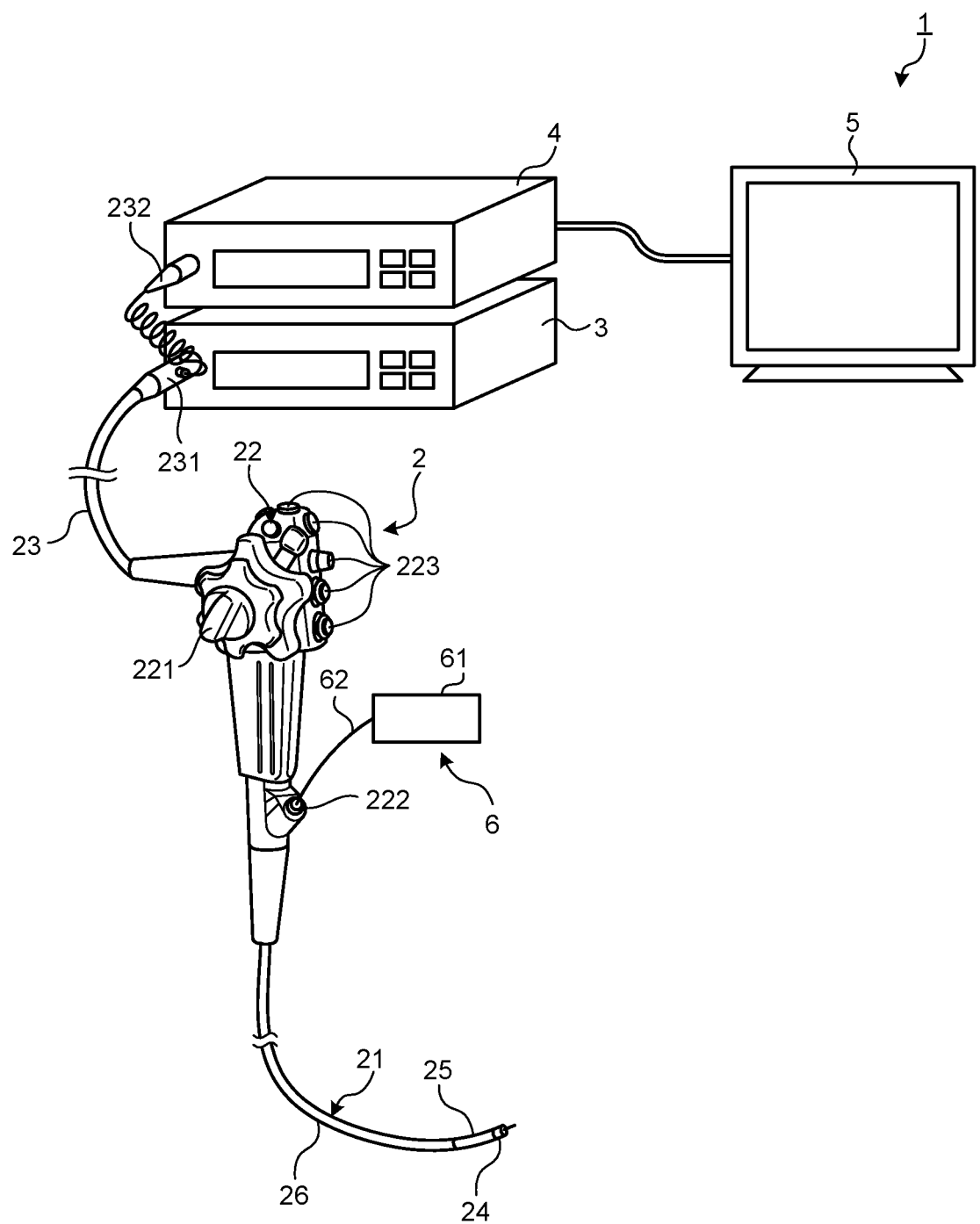
FIG. 1 is a diagram illustrating a schematic configuration of an endoscope system according to a first embodiment of the present invention.
Figure 2:
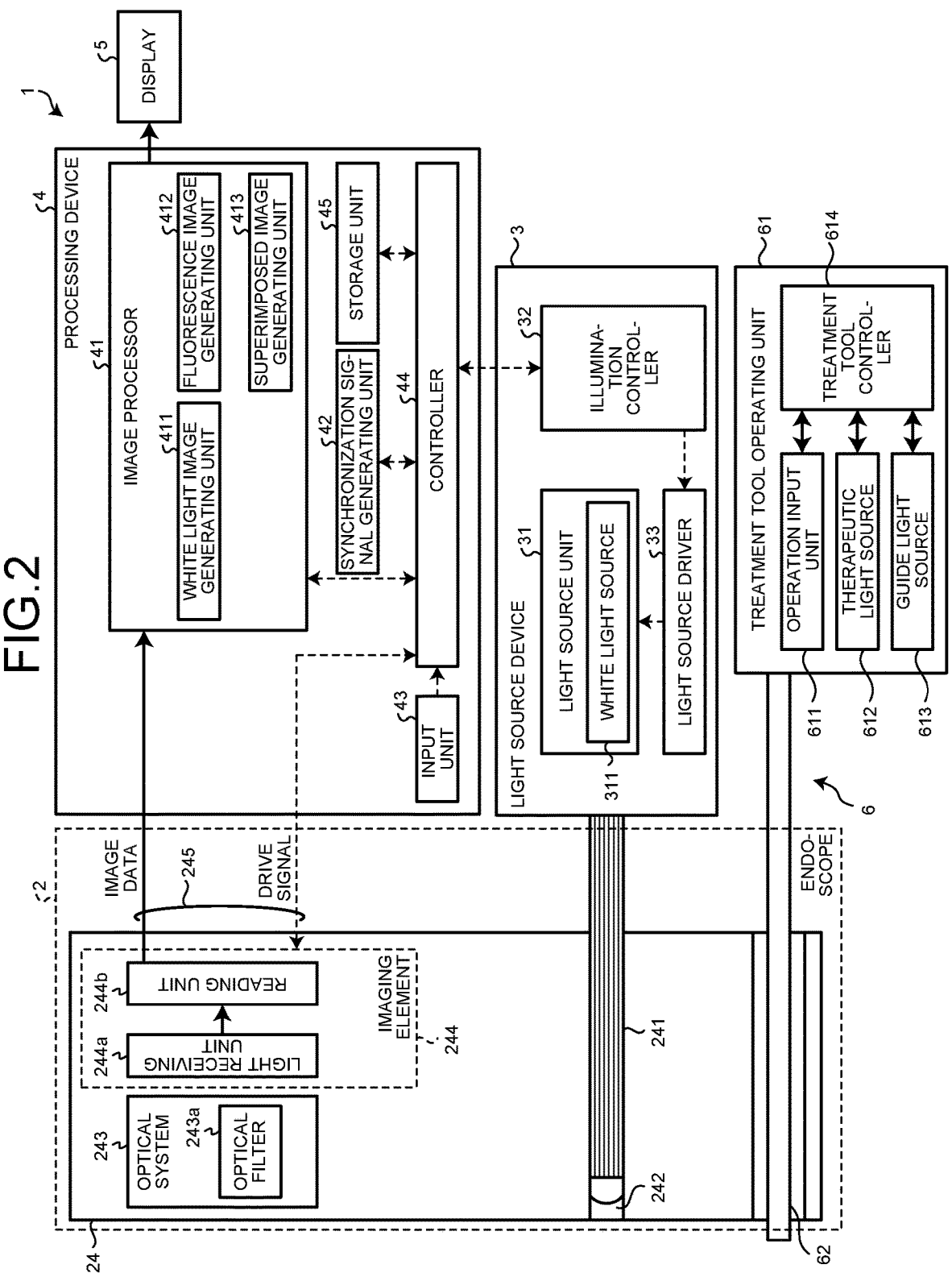
FIG. 2 is a block diagram illustrating a schematic configuration of the endoscope system according to the first embodiment of the present invention.
Figure 3:
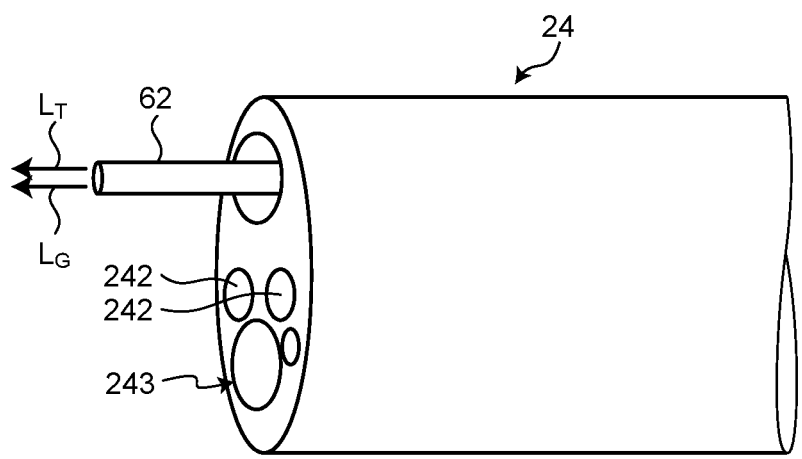
FIG. 3 is a diagram explaining a distal end structure of the endoscope device according to the first embodiment of the present invention.

FIG. 1 is a diagram illustrating a schematic configuration of an endoscope system according to a first embodiment of the present invention. FIG. 2 is a block diagram illustrating a schematic configuration of the endoscope system according to the first embodiment. FIG. 3 is a diagram explaining a distal end structure of an endoscope according to the present embodiment.

The endoscope system 1 illustrated in FIGS. 1 and 2 includes: an endoscope 2 that captures an in-vivo image of a subject by insertion of a distal end portion in the subject; a light source device 3 that generates illumination light to be emitted from the distal end of the endoscope 2; a processing device 4 that performs predetermined signal processing on an imaging signal captured by the endoscope 2 and integrally controls overall operation of the endoscope system 1; a display 5 that displays the in-vivo image generated by the signal processing by the processing device 4, and a treatment device 6.

The endoscope 2 includes: an insertion unit 21 that is flexible and has a long thin shape; an operating unit 22 connected to a proximal end side of the insertion unit 21 and receives input of various operation signals; and a universal cord 23 extending in a different direction from a direction in which the insertion unit 21 extends from the operating unit 22 and incorporates various cables connected to the light source device 3 and the processing device 4.

The insertion unit 21 includes: a distal end portion 24 incorporating an imaging element 244 in which pixels that receive light and generate a signal by performing photoelectric conversion are arrayed in a two-dimensional shape; a bending unit 25 freely bendable, the bending unit including a plurality of bending pieces; and a flexible tube unit 26 connected to a proximal end side of the bending unit 25, the flexible tube unit 26 being flexible and having a long shape. The insertion unit 21 is inserted in a body cavity of a subject and captures, by the imaging element 244, an object such as a biological tissue at a position where external light dose not reach.

The operating unit 22 includes: a bending knob 221 that causes the bending unit 25 to bend in the vertical direction and the horizontal direction; a treatment tool insertion unit 222 from which a treatment tool such as a therapeutic light irradiation device, biopsy forceps, an electric scalpel, and an inspection probe is inserted in a body cavity of a subject; and a plurality of switches 223 which are operation input units for inputting an operation instruction signal of peripheral devices such as an air delivering unit, a water delivering unit, and a screen display control in addition to the processing device 4. A treatment tool inserted from the treatment tool insertion unit 222 is exposed from an opening via a treatment tool channel (not illustrated) of the distal end portion 24 (see FIG. 3).

The universal cord 23 incorporates at least a light guide 241 and a collective cable 245 in which one or more signal lines are bundled. The universal cord 23 branches at an end opposite to a side connected to the operating unit 22. A connector 231 detachable from the light source device 3 and a connector 232 detachable from the processing device 4 are provided at the branching end of the universal cord 23. A part of the light guide 241 extends from the end of the connector 231. The universal cord 23 propagates illumination light emitted from the light source device 3 to the distal end portion 24 via the connector 231 (light guide 241), the operating unit 22, and the flexible tube unit 26. The universal cord 23 also transmits an image signal captured by the imaging element 244 included at the distal end portion 24 to the processing device 4 via the connector 232. The collective cable 245 includes a signal line for transmitting an imaging signal, a signal line for transmitting a driving signal for driving the imaging element 244, and a signal line for transmitting and receiving information including unique information related to the endoscope 2 (imaging element 244). Note that, in the present embodiment, description is given on the premise that an electric signal is transmitted using a signal line, however, an optical signal may be transmitted, or a signal may be transmitted between the endoscope 2 and the processing device 4 by wireless communication.

The distal end portion 24 includes: the light guide 241 formed by a glass fiber or the like and forming a light guiding path of light emitted by the light source device 3; an illumination lens 242 provided at the distal end of the light guide 241; an optical system 243 for condensing light; and the imaging element 244 which is included at an image formation position of the optical system 243, receives light condensed by the optical system 243, photoelectrically converts the light into an electric signal, and performs predetermined signal processing. Note that the optical system 243 and the imaging element 244 are include in an imager.

The optical system 243 includes one or more lenses. The optical system 243 forms an observation image on a light receiving surface of the imaging element 244. The optical system 243 includes an optical filter 243a. The optical characteristics of the optical filter 243a will be described later. Note that the optical system 243 may have an optical zoom function of changing the angle of view and a focus function of changing the focus.

The imaging element 244 performs photoelectric conversion on light from the optical system 243 and thereby generates an electric signal (imaging signal). The imaging element 244 includes a plurality of pixels arranged in a matrix shape, each of the pixels including a photodiode that accumulates electric charge corresponding to the amount of light, a capacitor that converts electric charge transferred from the photodiode into a voltage level, and others. The imaging element 244 generates an electric signal by photoelectrically converting light incident on each of the pixels via the optical system 243, sequentially reads the electric signals generated by pixels desirably set as reading targets among the plurality of pixels, and outputs the electric signals as imaging signals. The imaging element 244 is implemented by using, for example, a charge coupled device (CCD) image sensor, or a complementary metal oxide semiconductor (CMOS) image sensor.

Note that the endoscope 2 includes a memory (not illustrated) that stores an execution program and a control program for the imaging element 244 to execute various operations and data including identification information of the endoscope 2. The identification information includes unique information (ID), the year of manufacture, specifications information, the transmission scheme, or others of the endoscope 2. The memory may also temporarily store image data or the like generated by the imaging element 244.

Note that the endoscope 2 includes a memory (not illustrated) that stores an execution program and a control program for the imaging element 244 to execute various operations and data including identification information of the endoscope 2. The identification information includes unique information (ID), the year of manufacture, specifications information, the transmission scheme, or others of the endoscope 2. The memory may also temporarily store image data or the like generated by the imaging element 244.

Meanwhile, in the first embodiment, in the endoscope system 1, either a white image observation mode of observing an image obtained by illumination with white light or a fluorescence observation mode of observing a fluorescence image obtained by illumination with therapeutic light is set as an observation mode. Note that the fluorescence observation mode includes an in-treatment fluorescence observation mode and a pre-treatment and post-treatment fluorescence observation mode described later.

The configuration of the light source device 3 will be described. The light source device 3 includes a light source unit 31, an illumination controller 32, and a light source driver 33. The light source unit 31 includes a white light source 311 that emits illumination light under the control of the illumination controller 32.

The white light source 311 emits light (white light) having a visible wide wavelength band. The white light source 311 is implemented by an LED light source or any other light source such as a laser light source, a xenon lamp, or a halogen lamp. The white light source 311 may further include one or a plurality of lenses. The light generated by the white light source 311 is emitted toward an object from the distal end of the distal end portion 24 via the light guide 241.

The illumination controller 32 controls the amount of electric power supplied to the light source unit 31 and further controls a light source to cause emission of light or driving timing of a light source unit on the basis of a control signal (dimming signal) from the processing device 4.

The light source driver 33 supplies a current to a light source to be caused to emit light under control by the illumination controller 32 and thereby causes the light source unit 31 to emit light.

The configuration of the processing device 4 will be described. The processing device 4 includes an image processor 41, a synchronization signal generating unit 42, an input unit 43, a controller 44, and a storage unit 45.

The image processor 41 receives, from the endoscope 2, imaging signals captured by the imaging element 244 and including image data of illumination light of multiple colors. When receiving analog image data from the endoscope 2, the image processor 41 performs A/D conversion to generate digital signals. Alternatively, in a case where image data is received as optical signals from the endoscope 2, the image processor 41 performs photoelectric conversion to generate digital image data. The image processor 41 processes the received imaging signals and generates an image to be displayed on the display 5.

The image processor 41 performs predetermined image processing on the image data received from the endoscope 2 to generate an image and outputs the image to the display 5. The image processor 41 includes a white light image generating unit 411, a fluorescence image generating unit 412, and a superimposed image generating unit 413.

The white light image generating unit 411 generates a white light image based on an image formed by white light. The white light image generating unit 411 generates an image on the basis of signals captured at timing when the white light is being emitted.

The fluorescence image generating unit 412 generates a fluorescence image based on an image formed by fluorescence. The fluorescence is emitted when the antibody drug is excited, for example, by irradiation with therapeutic light. The fluorescence image generating unit 412 generates an image on the basis of signals captured at the timing when the therapeutic light is emitted.

The white light image generating unit 411 and the fluorescence image generating unit 412 generate an image by performing predetermined image processing. Incidentally, the predetermined image processing includes synchronization processing, gradation correction processing, color correction processing, and others. The synchronization processing is processing of synchronizing image data of respective color components of RGB. The gradation correction processing is processing of correcting gradation of image data. The color correction processing is processing of performing color tone correction on image data. Note that the white light image generating unit 411 and the fluorescence image generating unit 412 may perform gain adjustment depending on the brightness of the image.

The superimposed image generating unit 413 generates a superimposed image in which a fluorescence image is superimposed on a white light image. For example, the superimposed image generating unit 413 performs superimposition processing on the white light image and the fluorescence image of adjacent imaging frames at close imaging times.

The white light image generating unit 411, the fluorescence image generating unit 412, and the superimposed image generating unit 413 execute processing in accordance with a set observation mode. For example, in a case where the white image observation mode is set, a white light image is generated. Meanwhile, in a case where the fluorescence observation mode is set, a superimposed image and/or a fluorescence image is generated.

The image processor 41 includes a general-purpose processor such as a central processing unit (CPU) or a dedicated processor such as various arithmetic circuits that execute specific functions such as an application specific integrated circuit (ASIC). Note that the image processor 41 may include a frame memory that holds R image data, G image data, and B image data.

The synchronization signal generating unit 42 generates a clock signal (synchronization signal) serving as a reference of operation of the processing device 4 and outputs the generated synchronization signal to the light source device 3, the image processor 41, the controller 44, and the endoscope 2. Incidentally, the synchronization signal generated by the synchronization signal generating unit 42 includes a horizontal synchronization signal and a vertical synchronization signal.

Therefore, the light source device 3, the image processor 41, the controller 44, and the endoscope 2 operate in synchronization with each other by the generated synchronization signal.

The input unit 43 is implemented by using a keyboard, a mouse, a switch, or a touch panel and receives input of various signals such as an operation instruction signal that instructs the operation of the endoscope system 1. Note that the input unit 43 may include a switch included in the operating unit 22 or a portable terminal such as an external tablet computer.

The controller 44 performs driving control of components including the imaging element 244 and the light source device 3 and input and output control of information with each component. The controller 44 refers to control information data (e.g. reading timing) for imaging control stored in the storage unit 45 and transmits the data to the imaging element 244 via a predetermined signal line included in the collective cable 245 as a driving signal. The controller 44 also sets and switches the observation mode. The controller 44 sets any one of the white image observation mode, the in-treatment fluorescence observation mode, or the pre-treatment and post-treatment fluorescence observation mode on the basis of, for example, operation input by an operator or the like. In the first embodiment, an example in which the in-treatment fluorescence observation mode is set as the fluorescence observation mode will be described. The controller 44 includes a general-purpose processor such as a CPU or a dedicated processor such as various arithmetic circuits that execute specific functions such as an ASIC.

The storage unit 45 stores data including various programs for causing the endoscope system 1 to operate and various parameters required for operation of the endoscope system 1. The storage unit 45 further stores identification information of the processing device 4. Incidentally, the identification information includes unique information (ID) of the processing device 4, the year of manufacture, specifications information, or others.

In addition, the storage unit 45 stores various programs including an image acquisition processing program for executing an image acquisition processing method of the processing device 4. The various programs can be recorded on a computer-readable recording medium such as a hard disk, a flash memory, a CD-ROM, a DVD-ROM, or a flexible disk and be widely distributed. Note that the above-described various programs can also be acquired by being downloaded via a communication network. The communication network referred to here is implemented by, for example, an existing public line network, a local area network (LAN), a wide area network (WAN), or the like and may be either wired or wireless.

The storage unit 45 having the above configuration is implemented by using a read only memory (ROM) in which the various programs and the like are installed in advance, a RAM, a hard disk, or the like that store calculation parameters, data, and the like of each processing.

The display 5 displays a display image corresponding to image signals received from the processing device 4 (image processor 41) via a video cable. The display 5 includes a monitor of, for example, liquid crystal or organic electroluminescence (EL).

The treatment device 6 includes a treatment tool operating unit 61 and a flexible treatment tool 62 extending from the treatment tool operating unit 61. The treatment tool 62 used in the PIT is a therapeutic light emission unit that emits light for treatment (hereinafter, referred to as therapeutic light).

The treatment tool operating unit 61 controls emission of light from the treatment tool 62.

The treatment tool operating unit 61 includes an operation input unit 611, a therapeutic light source 612, a guide light source 613, and a treatment tool controller 614. Each light source is implemented using a semiconductor laser, an LED, or the like. Note that, in the treatment device 6, the light source that emits the therapeutic light may be included in the treatment tool 62 or may be included in the treatment tool operating unit 61.

The operation input unit 611 includes, for example, a switch or the like. The treatment tool operating unit 61 causes the treatment tool 62 to emit therapeutic light or guide light by input to the operation input unit 611 (for example, pressing the switch).

The therapeutic light source 612 includes a light source or one or more lenses and emits light (illumination light) when the light source is driven. The light source included in the therapeutic light source 612 emits light in a wavelength band for exciting the antibody drug. For example, in the case of the PIT, the therapeutic light is light in a wavelength band higher than or equal to 680 nm and is light having a center wavelength of 690 nm, for example.

The guide light source 613 includes a light source or one or more lenses and emits light (illumination light) when the light source is driven. The light source included in the guide light source 613 emits light having a wavelength band shorter than the wavelength band of the light emitted from the therapeutic light source 612 and shorter than the wavelength band blocked by the optical filter 243a.

An illumination light system included in the treatment tool 62 emits the therapeutic light and the guide light in a mode in which the irradiation positions of the therapeutic light and the guide light are the same. For example, the irradiation area of the therapeutic light and the irradiation area of the guide light substantially coincide with each other.

Note that the illumination light system included in the treatment tool 62 may be configured so as to be able to change the irradiation range of the therapeutic light. For example, under the control of the treatment tool operating unit 61, it is possible to include an optical system capable of changing the focal length, a digital micromirror device (DMD), or the like and to change the spot diameter of the light, with which an object is irradiated, or the shape of the irradiation range.

The treatment tool controller 614 performs driving control of components including the operation input unit 611, the therapeutic light source 612, and the guide light source 613 as well as input and output control of information with the components. For example, the treatment tool controller 614 causes the therapeutic light source 612 or the guide light source 613 to emit light on the basis of an operation input by the operator or the like. The treatment tool controller 614 includes a general-purpose processor such as a CPU or a dedicated processor such as various arithmetic circuits that execute specific functions such as an ASIC.

Here, characteristics of the therapeutic light, the antibody drug, the fluorescence, and the optical filter 243a will be described with reference to FIGS. 4 and 5.

Figure 4:
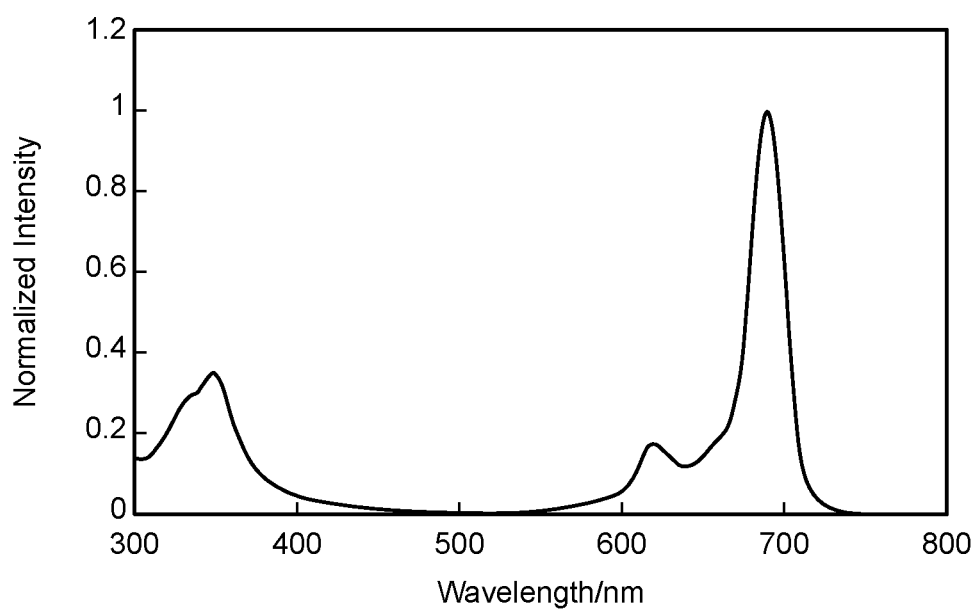
FIG. 4 is a graph illustrating an example of an absorption spectrum of therapeutic light.

FIG. 4 is a graph illustrating an absorption spectrum of the antibody drug. In FIG. 4, an absorption spectrum of IRDye (registered trademark) 700DX is illustrated as an example of the antibody drug. In FIG. 4, illustrated in the normalized intensity obtained by normalizing using the intensity of the maximum peak as 1. IRDye (registered trademark) 700DX has a first light absorption band with a peak at 690 nm in a wavelength band greater than or equal to 650 nm and a second light absorption band with a peak at 350 nm in a wavelength band of less than 450 nm. In particular, the first light absorption band corresponds to a wavelength band to be a target for causing the antibody drug to react when phototherapy is performed. Note that the second light absorption band may be also referred to as a Soret band.

Figure 5:
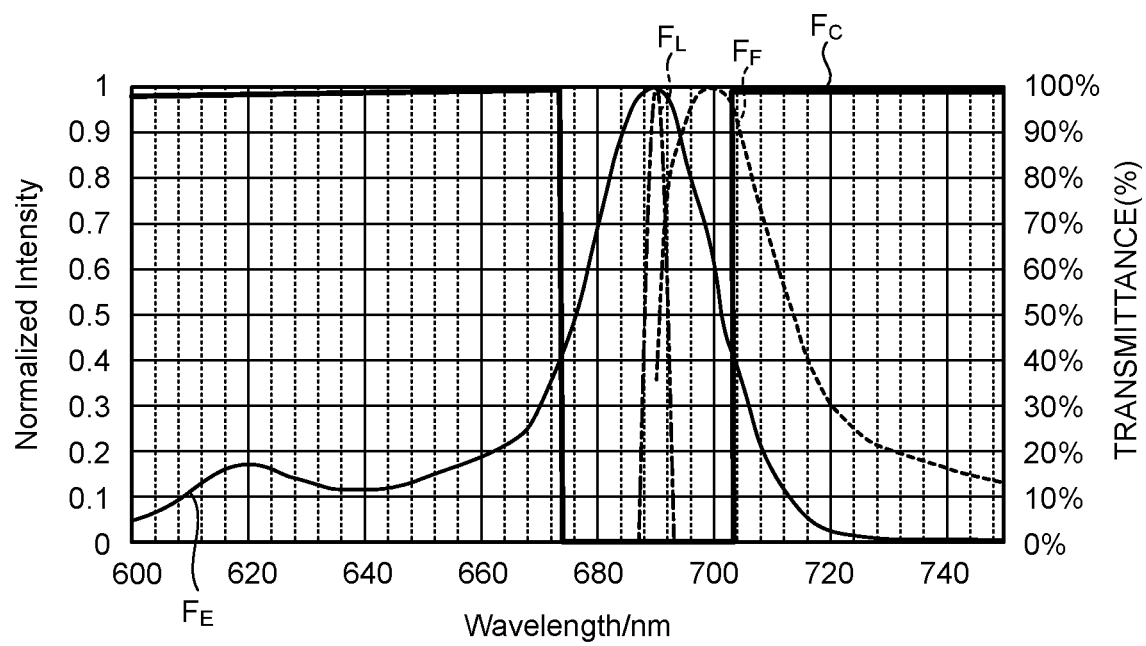
FIG. 5 is a graph illustrating an example of an excitation spectrum and a fluorescence spectrum of an antibody drug, a wavelength spectrum of therapeutic light, and transmission characteristics of an optical filter.

FIG. 5 is a graph illustrating an example of an excitation spectrum and a fluorescence spectrum of the antibody drug, a wavelength spectrum of therapeutic light, and transmission characteristics of the optical filter. In FIG. 5, a curve $F_E$ indicates absorption characteristics of IRDye (registered trademark) 700DX (see FIG. 4). A curve $F_L$ indicates an intensity distribution of a laser beam emitted as the therapeutic light. A curve $F_F$ indicates an intensity distribution of fluorescence generated by excitation of the antibody drug. A curve $F_C$ indicates absorption characteristics (transmittance) of the optical filter 243a. In FIG. 5, the curves $F_E$, $F_L$, and $F_F$ indicate the normalized intensity obtained by normalizing the respective curves using the intensity of the maximum peak as 1.

The optical filter 243a has absorption characteristics indicated by the curve $F_C$. That is, the wavelength band of the optical filter 243a is set in consideration of the tolerance of the center wavelength of the therapeutic light source 612 around 690 nm, the spectral width, and oblique incidence characteristics to the optical filter 243a in the optical system of the optical filter 243a. For example, light in a wavelength band greater than 670 nm and less than 700 nm is blocked, and light in other wavelength bands is transmitted.

The light in the above range is cut by the optical filter 243a with respect to the light incident from the distal end portion 24. For example, due to the characteristics of the optical filter 243a, light in the wavelength band of the therapeutic light is not incident on the imaging element 244, and fluorescence is incident on the imaging element 244.

Figure 6:
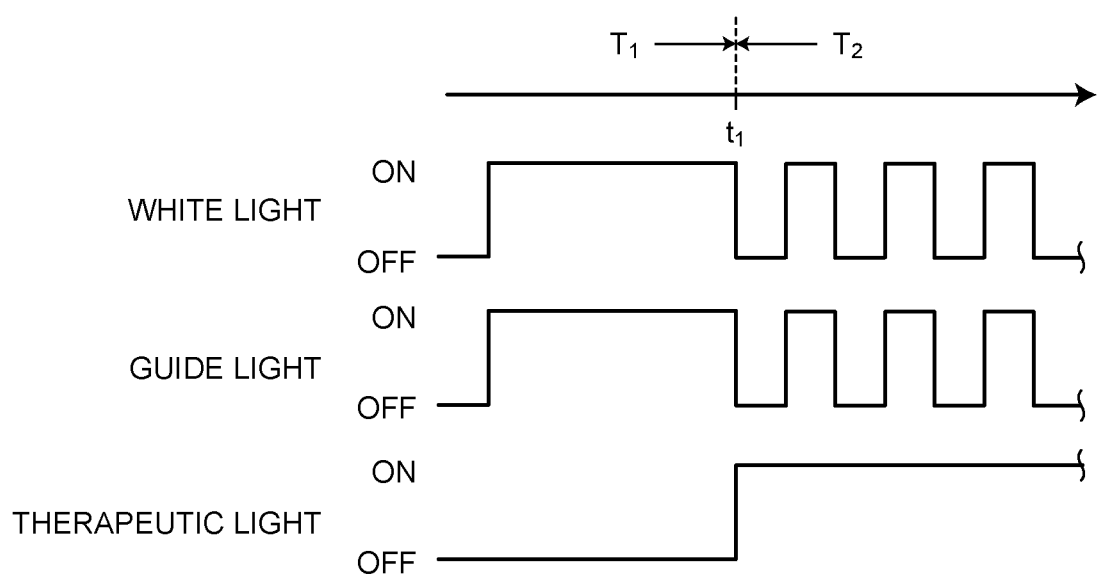
FIG. 6 is a diagram for explaining ON and OFF timings of white light, guide light, and therapeutic light according to the first embodiment of the present invention.

Next, image acquisition at the time of treatment using the endoscope 2 will be described with reference to FIGS. 6 to 9. FIG. 6 is a diagram for explaining ON and OFF timings of white light, guide light, and the therapeutic light according to the first embodiment of the present invention. Hereinafter, an example of implementation of the PIT will be described. For example, the insertion unit 21 is inserted into an upper gastrointestinal tract to treat a target site.

While the treatment position is searched, the observation mode is set to the white image observation mode, and white light and guide light are emitted (period $T_1$ in FIG. 6). In this period, white light and guide light are continuously emitted. While the treatment position is searched for, the observation mode is set to the white image observation mode, and a white light image based on the white light and the guide light is generated. Meanwhile, when operation input is made to the treatment tool 62 at time $t_1$ and the therapeutic light source is turned on, white light and guide light are intermittently emitted at predetermined intervals (period $T_2$ in FIG. 6). For example, the observation mode is switched to the in-treatment fluorescence observation mode on the basis of input of an ON instruction for the therapeutic light. At this point, the therapeutic light is continuously emitted. By irradiation with the therapeutic light, the antibody drug is excited, and the target site is treated.

In the first embodiment, the controller 44 of the processing device 4 serves as a control master to control the emission timings of the white light source 311 and the guide light source 613 and to control the imaging timing of the imaging element 244. Meanwhile, the therapeutic light source 612 is driven asynchronously with the white light and the guide light under the control of the treatment tool controller 614. When the lighting control of the therapeutic light source 612 is executed by the input to the operation input unit 611, the controller 44 switches to the in-treatment fluorescence observation mode, executes the intermittent emission control of the white light and the guide light, and causes the fluorescence image generating unit 412 and the superimposed image generating unit 413 to execute image generation processing.

At the time of treatment, specifically, for example, the operator first administers the antibody drug intravenously by drip infusion using an injection 20 to 28 hours before the treatment (surgery). Note that the administration of the antibody drug may be performed using the endoscope 2, may be performed using another device, or may be performed by orally administering the drug to the patient.

Then, the operator inserts the insertion unit 21 into the upper gastrointestinal tract. At this point, the observation mode is set to the white image observation mode, and the operator causes the light source device 3 to emit white light, further causes the treatment tool 62 to protrude from the distal end of the endoscope 2 and to emit guide light to the treatment tool 62, and searches for the treatment position while observing the white light image of the inside of the upper gastrointestinal tract displayed by the display 5. At this point, the guide light is visualized in the white light image, and the irradiation position of the therapeutic light is guided by the guide light.

Figure 7:
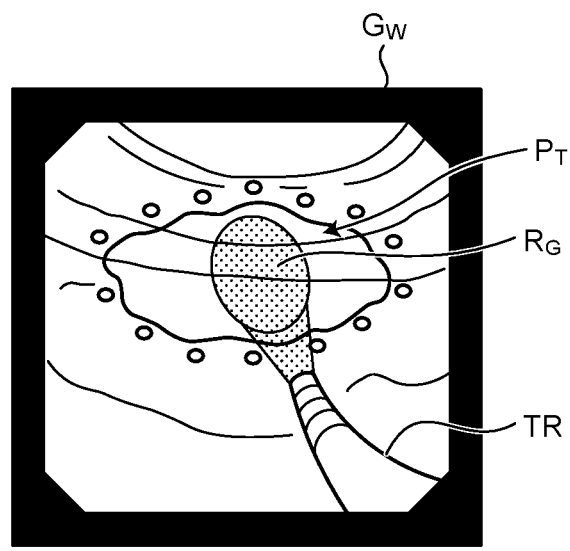
FIG. 7 is a diagram illustrating an example of a white light image.

FIG. 7 is a diagram illustrating an example of a white light image. In the white image observation mode, for example, a white light image $G_W$ is displayed on the display 5. In the white light image $G_W$, by reflection light or scattered light of the white light, the tissue of an observation region including the treatment target site or an image TR of the treatment tool 62 is visualized, and an irradiation range $R_G$ of the guide light is visualized. The operator searches for the target site and adjusts the irradiation position of the therapeutic light while observing the irradiation area of the guide light. The operator adjusts the irradiation position of the therapeutic light to the target site by, for example, adjusting the orientation of the distal end portion 24 or adjusting the protruding length of the treatment tool 62.

After adjusting the orientation of the distal end portion 24 or others, the operator irradiates the target site with the therapeutic light. By irradiation with the therapeutic light, the antibody drug bound to a target site $P_T$ reacts, thereby performing treatment on the target site. During the irradiation with the therapeutic light, the observation mode is set to the in-treatment fluorescence observation mode, a fluorescence image is generated on the basis of a fluorescence image acquired while the white light and the guide light are not emitted, and a superimposed image is generated from the fluorescence image and the white light image. The generated image is displayed on the display 5. The operator confirms the therapeutic effect by observing the intensity of fluorescence, the emission region, and the like.

Figure 8:
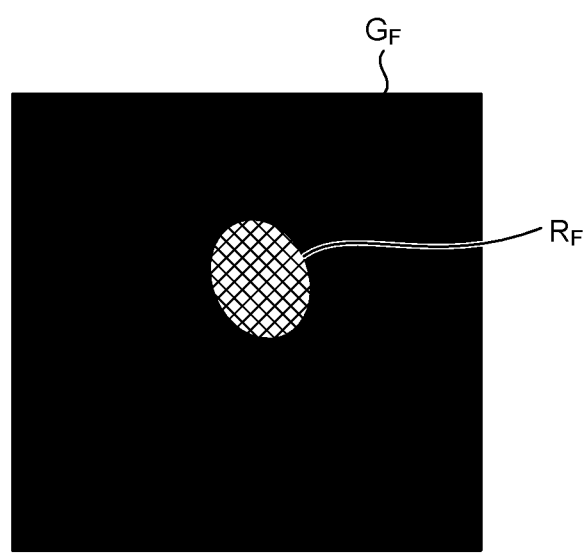
FIG. 8 is a diagram illustrating an example of a fluorescence image.

FIG. 8 is a diagram illustrating an example of a fluorescence image. In a fluorescence image $G_F$ illustrated in FIG. 8, a fluorescence image $R_F$ is visualized. At this point, since excitation light (here, the therapeutic light) is cut by the optical filter 243a, the excitation light is not visualized as an image.

Figure 9:
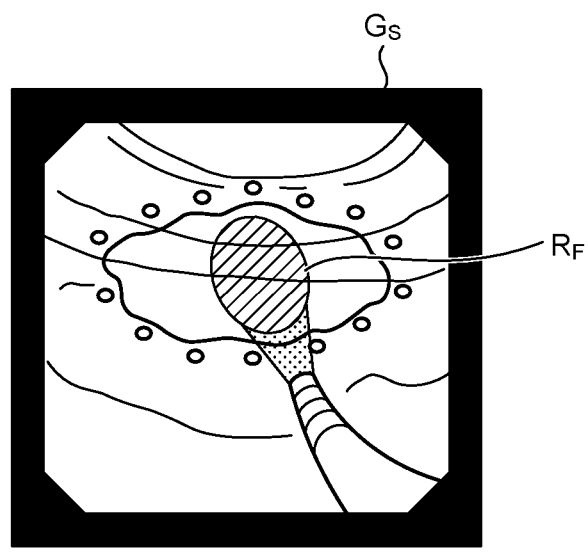
FIG. 9 is a diagram illustrating an example of a superimposed image in which a fluorescence image is superimposed on a white light image.

FIG. 9 is a diagram illustrating an example of a superimposed image in which a fluorescence image is superimposed on a white light image. The superimposed image generating unit 413 increases the brightness of the fluorescence image with respect to the brightness of the white light image at a predetermined ratio, for example, four times brighter than that of the white light image and superimposes the fluorescence image on the white light image in a state where the fluorescence image is enhanced. At this point, since the fluorescence intensity is used for determination of the therapeutic effect, the enhancement degree of the brightness is set to be the same for an image of the same observed region, and as processing in which the brightness of the fluorescence image does not change by image processing, it is made clear how the fluorescence image becomes dark with elapse of time. A superimposed image $G_S$ illustrated in FIG. 9 is an image in which the fluorescence image $R_F$ is superimposed on the white light image $G_W$.

The operator treats the target site by repeating additional irradiation with the therapeutic light and confirmation of the treatment effect, as necessary.

In the first embodiment described above, for acquiring a white light image, the guide light, which has a shorter wavelength than that of the therapeutic light and irradiates substantially the same region as the therapeutic light does, is emitted together with the white light, whereas, for acquiring a fluorescence image, the white light and the guide light are turned off, and a fluorescence image in which the excitation light is cut by the optical filter 243a is generated. According to the first embodiment, in the white light image, the irradiation area of the therapeutic light is guided by the guide light, and the superimposed image in which the fluorescence image including only fluorescence images is superimposed on the white light image is generated, and thus observation of the target site can be continued even at the time of fluorescence observation. Furthermore, according to the first embodiment, since one sheet of imaging element 244 is included, and the excitation light incident on the imaging element 244 is cut by the optical filter 243a, it is possible to prevent an increase in the diameter as compared with a configuration using two sheets of imaging elements.

Note that, in the first embodiment, an example in which the optical filter 243a is included in the optical system 243 has been described. However, the optical filter 243a may be included on a light receiving surface side of a light receiving unit 244a in the imaging element 244.

First Modification of First Embodiment

Next, a first modification of the first embodiment will be described. Since an endoscope system according to the first modification is the same as the endoscope system 1 according to the first embodiment, the description thereof will be omitted. In the first embodiment, the example in which the controller 44 serves as a control master to control the guide light source 613 and the like has been described, however, in a first modification, the treatment tool controller 614 serves as a control master to control the guide light source 613 and others.

Note that the flow of treatment using the endoscope system is similar to that of the first embodiment.

In the first modification, the treatment tool controller 614 of the treatment device 6 serves as a control master to control the emission timings of the white light source 311 and the guide light source 613 and to control the imaging timing of the imaging element 244. Meanwhile, the therapeutic light source 612 is driven asynchronously with the white light and the guide light under the control of the treatment tool controller 614. Simultaneously with execution of lighting control of the therapeutic light source 612 by input to the operation input unit 611, the treatment tool controller 614 switches to the in-treatment fluorescence observation mode, causes the controller 44 to execute intermittent emission control of the white light and the guide light, and causes the fluorescence image generating unit 412 and the superimposed image generating unit 413 to execute image generation processing.

In the first modification described above, like in the first embodiment, for acquiring a white light image, the guide light is emitted together with the white light, whereas, for acquiring a fluorescence image, the white light and the guide light are turned off, and a fluorescence image in which the excitation light is cut by the optical filter 243a is generated. According to the first modification, even in a case where the treatment tool controller 614 functions as the control master, observation of a target site can be continued even at the time of fluorescence observation. Furthermore, according to the first modification, like in the first embodiment, one sheet of imaging element 244 is included, and the excitation light incident on the imaging element 244 is cut by the optical filter 243a, and thus it is possible to prevent an increase in the diameter as compared with a configuration using two sheets of imaging elements.

Second Modification of First Embodiment

Next, a second modification of the first embodiment will be described. Since an endoscope system according to the second modification is the same as the endoscope system 1 according to the first embodiment, the description thereof will be omitted.

Note that the flow of treatment using the endoscope system is similar to that of the first embodiment.

Figure 10:
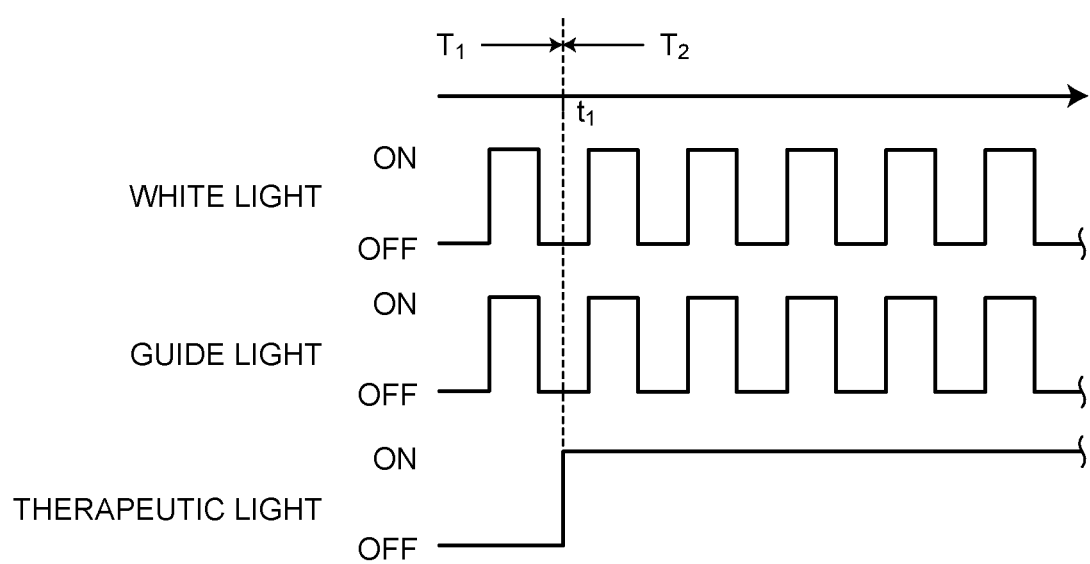
FIG. 10 is a diagram for explaining ON and OFF timings of white light, guide light, and therapeutic light according to a second modification of the first embodiment of the present invention.

FIG. 10 is a diagram for explaining ON and OFF timings of white light, guide light, and therapeutic light according to a second modification. First, the in-treatment fluorescence observation mode is set, and then white light and guide light are emitted until the therapeutic light is turned on (period $T_1$ in FIG. 10). In the second modification, in this period $T_1$, white light and guide light are intermittently emitted. Thereafter, at time $t_1$, operation input is made to the treatment tool 62, and the therapeutic light source is turned on (period $T_2$ in FIG. 10), and then the antibody drug is excited by irradiation with the therapeutic light, and the treatment of a target site is performed.

In the second modification, in the image processor 41, the white light image generating unit 411 generates a white light image by using signals captured during the period in which the white light and the guide light has been on until the time $t_1$ at which the therapeutic light is turned on. On the other hand, a completely dark image is obtained in the fluorescence image generating unit 412 since there is no signal of a fluorescence image, and a superimposed image generated in the superimposed image generating unit 413 includes only the white light image, and the white light image is displayed on the display 5. At this point, a threshold value is determined for signals in a fluorescence image, and the fluorescence image may not be enhanced in a case where the threshold value is not exceeded. When the therapeutic light is turned on at the time $t_1$, the white light image generating unit 411 generates the white light image using the signals captured during the period in which the white light and the guide light has been on, and the fluorescence image generating unit 412 generates a fluorescence image using signals captured during a period in which the therapeutic is been on. The superimposed image generating unit 413 superimposes the generated fluorescence image on the white light image to generate a superimposed image.

In the second modification described above, like in the first embodiment, for acquiring a white light image, the guide light is emitted together with the white light, whereas, for acquiring a fluorescence image, the fluorescence image is generated on the basis of an optical image in which the white light and the guide light are turned off and the excitation light is cut by the optical filter 243a. According to the second modification, the observation of the target site can be continued even at the time of fluorescence observation. Furthermore, according to the second modification, like in the first embodiment, one sheet of imaging element 244 is included, and the excitation light incident on the imaging element 244 is cut by the optical filter 243a, and thus it is possible to prevent an increase in the diameter as compared with a configuration using two sheets of imaging elements.

Third Modification of First Embodiment

Next, a third modification of the first embodiment will be described. Since an endoscope system according to the third modification is the same as the endoscope system 1 according to the first embodiment, the description thereof will be omitted. The third modification relates to observation of fluorescence images before treatment or after treatment, and description will be given with an example of processing before treatment. Note that the processing described below can also be applied after the treatment.

Note that the flow of treatment using the endoscope system is similar to that of the first embodiment.

Figure 11:
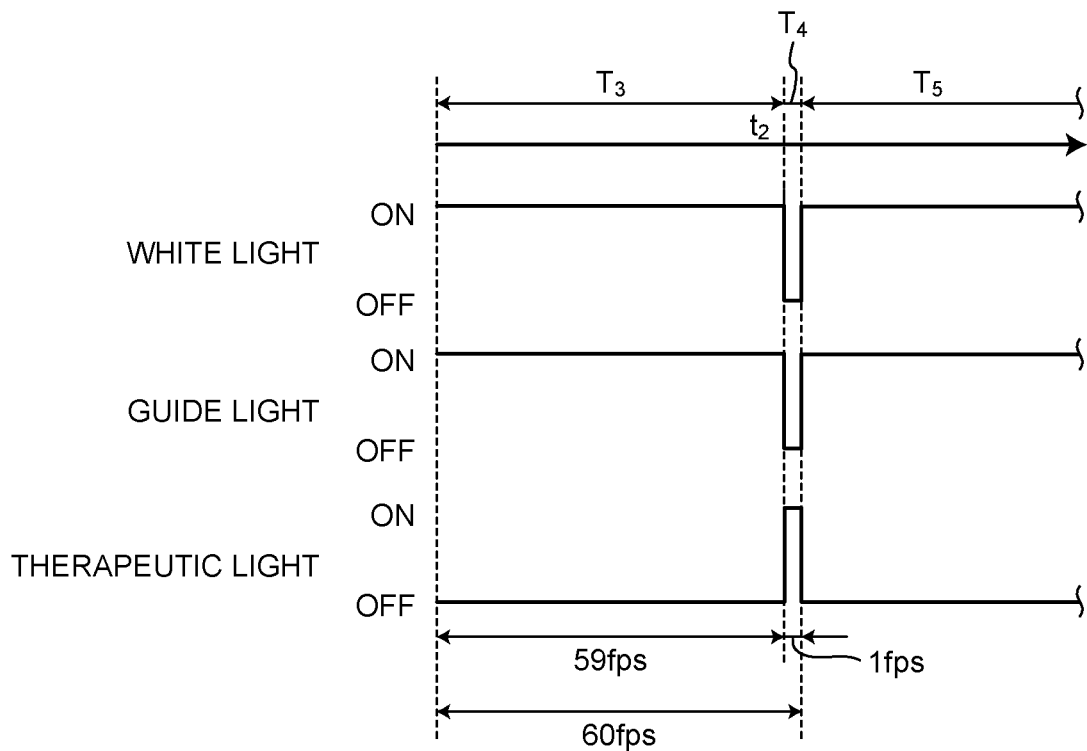
FIG. 11 is a diagram for explaining ON and OFF timings of white light, guide light, and therapeutic light according to a third modification of the first embodiment of the present invention.

FIG. 11 is a diagram for explaining ON and OFF timings of white light, guide light, and therapeutic light according to the third modification. Before starting the treatment, the mode is set to the pre-treatment and post-treatment fluorescence observation mode. In this mode, the controller 44 controls the white light source 311, the guide light source 613, and the therapeutic light source 612. When this mode is set, for example, in a case where imaging is performed at 60 fps, white light and guide light are emitted for 59 fps (period $T_3$ in FIG. 11). In the third modification, in this period $T_3$, white light and guide light are continuously emitted. Then, when the therapeutic light source is turned on via the treatment tool controller 614 under the control of the controller 44 at time $t_2$ of one frame for confirmation of the accumulation amount of the antibody drug or others, the fluorescence image generating unit 412 generates a fluorescence image. In the pre-treatment and post-treatment fluorescence observation mode, the therapeutic light is emitted for a time corresponding to one frame at 60 fps per second (period $T_4$ in FIG. 11), and the white light and the guide light are turned off. At this point, a superimposed image is displayed on the display 5, and the operator observes the fluorescence image. In a subsequent period $T_5$, the white light and the guide light are turned on again. Note that this pre-treatment and post-treatment fluorescence observation mode may be maintained until there is an instruction to set to the white image observation mode or other observation modes.

Here, in the pre-treatment and post-treatment fluorescence observation mode of the third modification, the therapeutic light is emitted only for a time corresponding to one frame, and a fluorescence image based on the therapeutic light is captured. Note that fluorescence observation (irradiation with the therapeutic light) can be performed a plurality of times intermittently up to a time limit.

In the third modification, in the pre-treatment and post-treatment fluorescence observation mode, in the image processor 41, the white light image generating unit 411 generates a white light image by using signals captured during the period in which the white light and the guide light are on. Meanwhile, the fluorescence image generating unit 412 generates a fluorescence image using signals captured during a period in which the therapeutic light has been on, and the white light image generating unit 411 generates the white light image using signals captured during the period in which the white light and the guide light are on. The superimposed image generating unit 413 superimposes the generated fluorescence image on the white light image to generate a superimposed image.

Figure 12:
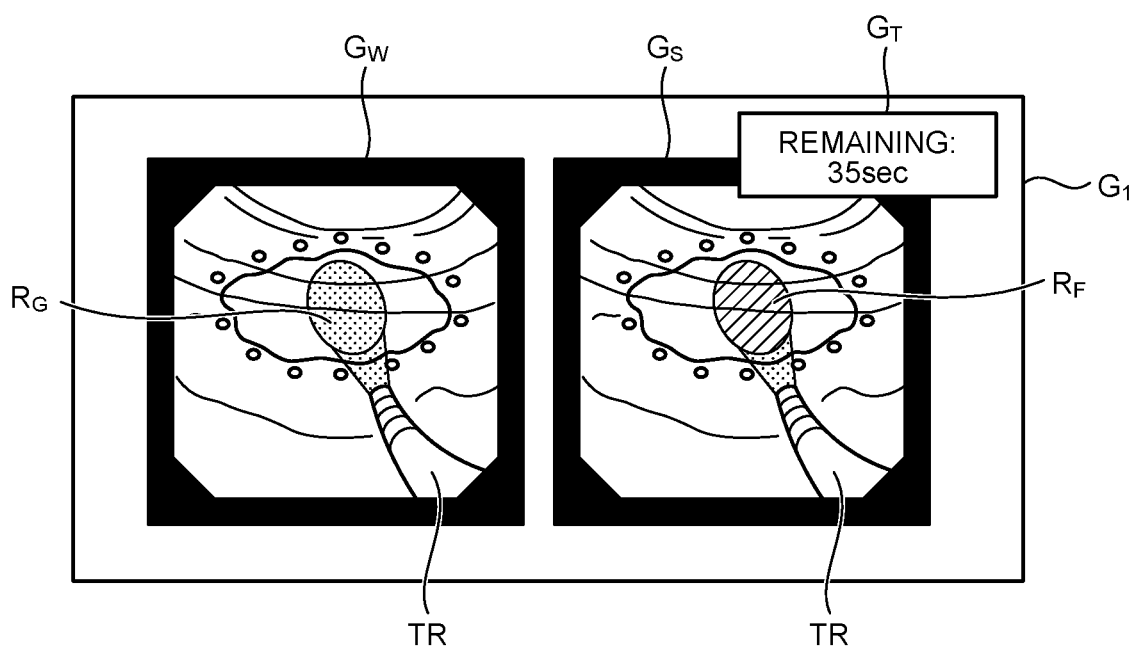
FIG. 12 is a diagram illustrating an example of a display image according to the third modification of the first embodiment of the present invention.

FIG. 12 is a diagram illustrating an example of a display image according to the third modification of the first embodiment of the present invention. In a display image $G_1$, the white light image $G_W$ and the superimposed image $G_S$ are displayed. At this point, since the white light image $G_W$ and the superimposed image $G_S$ are imaged at different timings, update timings of the images are different from each other. For example, in a period in which the fluorescence image mode is set, the white light image $G_W$ is updated at 59 fps, whereas the superimposed image $G_S$ is updated at 1 fps.

At this point, the effective period of the pre-treatment and post-treatment fluorescence observation mode may be displayed. For example, the remaining time after the instruction for the pre-treatment and post-treatment fluorescence observation mode has been first input, the remaining time of the effective period of this mode, is displayed on the effective period display unit $G_T$ illustrated in FIG. 12. Within this period, it is possible to observe the fluorescence image by repeatedly performing irradiation with the therapeutic light. On the other hand, when this effective period is over, for example, reception of irradiation with the therapeutic light is stopped before treatment.

In the third modification described above, for the treatment, like in the first embodiment, for acquiring a white light image, the guide light is emitted together with the white light, whereas, for acquiring a fluorescence image, the fluorescence image is generated on the basis of an optical image in which the white light and the guide light are turned off and the excitation light is cut by the optical filter 243a. According to the third modification, the observation of the target site can be continued even at the time of fluorescence observation. Furthermore, according to the third modification, like in the first embodiment, one sheet of imaging element 244 is included, and the excitation light incident on the imaging element 244 is cut by the optical filter 243a, and thus it is possible to prevent an increase in the diameter as compared with a configuration using two sheets of imaging elements.

In addition, according to the third modification, at the time of fluorescence observation (irradiation with therapeutic light) before and after the treatment, irradiation with the therapeutic light is performed only for a period corresponding to one frame, and thus it is possible to confirm a fluorescence image by the therapeutic light while treatment progress by the therapeutic light is suppressed.

Second Embodiment

Figure 13:
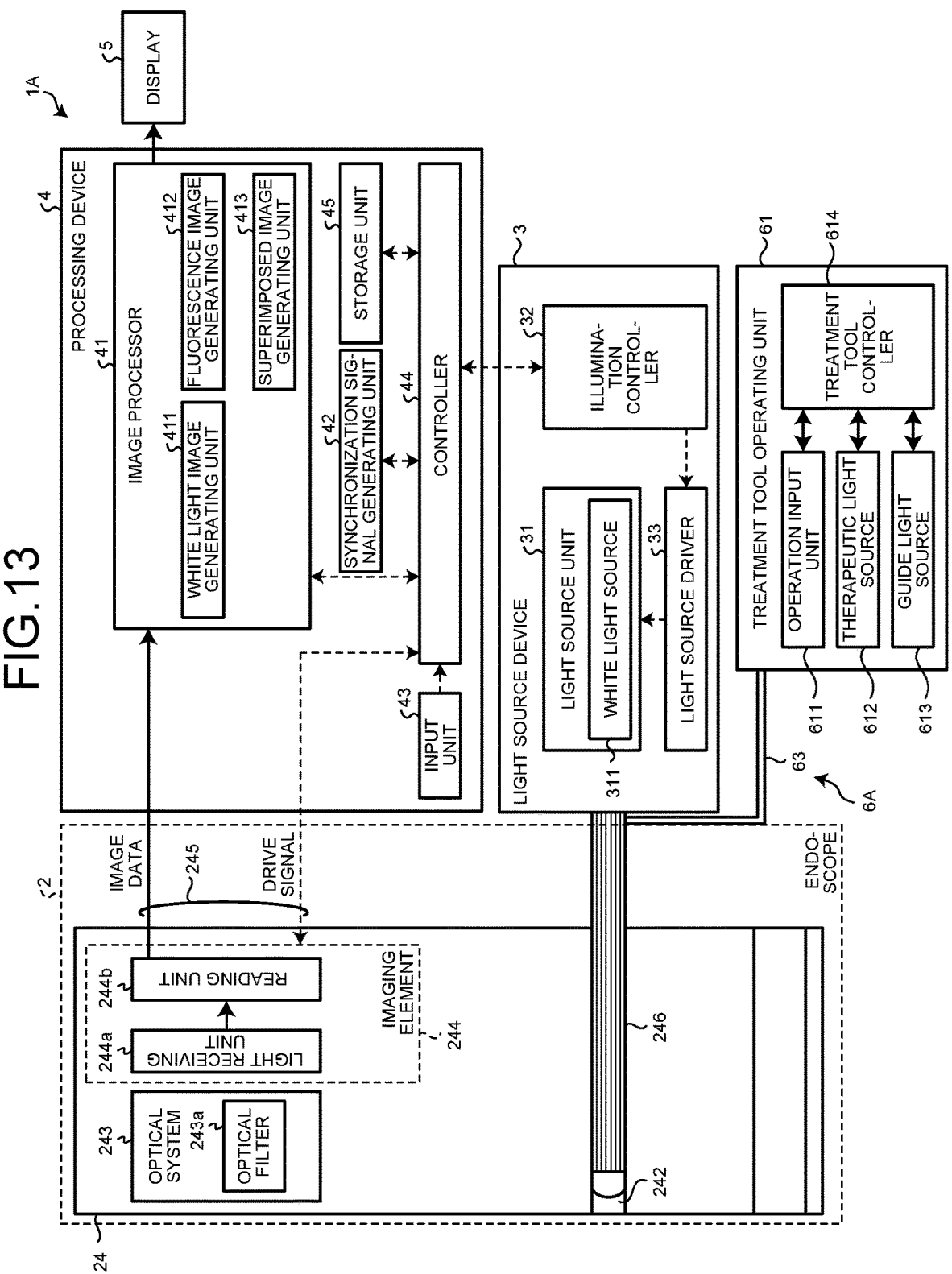
FIG. 13 is a block diagram illustrating a schematic configuration of an endoscope system according to a second embodiment of the present invention.

Next, a second embodiment will be described. In the second embodiment, the same components as those of the endoscope system 1 according to the first embodiment are denoted by the same symbols, and description thereof will be omitted. FIG. 13 is a block diagram illustrating a schematic configuration of an endoscope system according to the second embodiment of the present invention.

The endoscope system 1A illustrated in FIG. 13 includes: an endoscope 2 that captures an in-vivo image of a subject by insertion of a distal end portion in the subject; a light source device 3 that generates illumination light to be emitted from the distal end of the endoscope 2; a processing device 4 that performs predetermined signal processing on an imaging signal captured by the endoscope 2 and integrally controls overall operation of the endoscope device 1; a display 5 that displays the in-vivo image generated by the signal processing by the processing device 4, and a treatment device 6A. Note that the endoscope 2 will be described as including a first light guide 246 instead of the light guide 241.

The treatment device 6A includes a treatment tool operating unit 61 and a second light guide 63 extending from the treatment tool operating unit 61 and connected with the first light guide 246. The first light guide 246 and the second light guide 63 are included in a bifurcated light guide. The second light guide 63 may be connected to at least some fibers of the first light guide 246 or may extend to the distal end of a distal end portion 24 together with the first light guide 246.

The second light guide 63 transmits light emitted by a therapeutic light source 612 and a guide light source 613. At this point, the second light guide 63 emits light emitted by the therapeutic light source 612 and the guide light source 613 to the outside using, for example, shared fibers. Note that light emitted from each of the light sources may be transmitted using different fibers.

In addition, as light emitted from the distal end portion 24, a first irradiation range of light emitted from the white light source 311 is larger than a second irradiation range of light emitted from the therapeutic light source 612 and the guide light source 613, and the entire second irradiation range is included in the first irradiation range. The irradiation range of each ray of light can be adjusted by the incident angle on a fiber or the like. In addition, it is preferable that the entire second irradiation range fall within the angle of view of an image captured by the imaging element 244.

Figure 14:
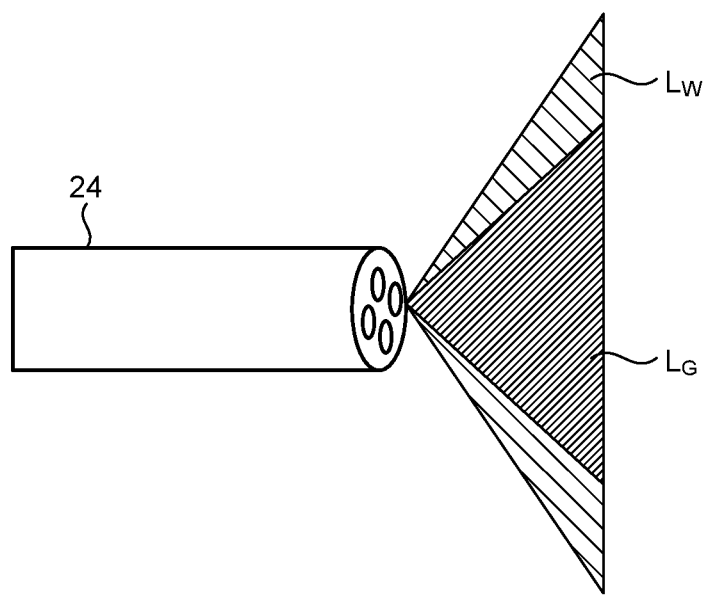
FIG. 14 is a diagram for explaining white light and guide light according to the second embodiment of the present invention.

FIG. 14 is a diagram for explaining white light and guide light according to the second embodiment of the present invention. FIG. 14 is a diagram schematically illustrating a cross section of light irradiation ranges in order to describe light irradiation ranges, the diagram illustrating a case where the white light $L_W$ and the guide light $L_G$ are emitted.

Figure 15:
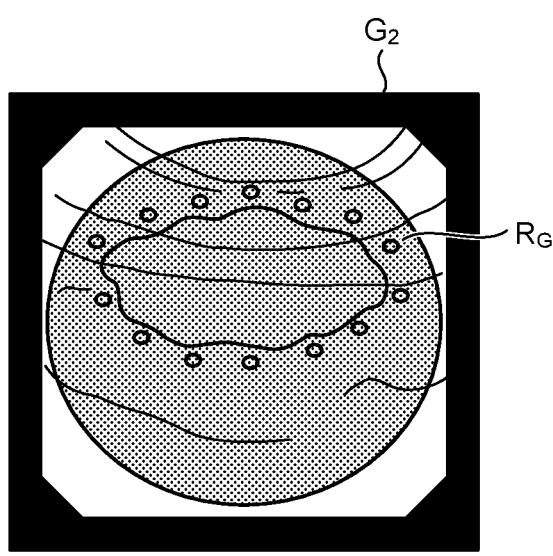
FIG. 15 is a diagram illustrating an example of a white light image.

FIG. 15 is a diagram illustrating an example of a white light image. In a white light image $G_2$, an irradiation range $R_G$ of guide light is visualized on a background including a tissue and others illuminated with white light. At this point, it is preferable that the irradiation range $R_G$ of the guide light falls within the white light image $G_2$.

Figure 16:
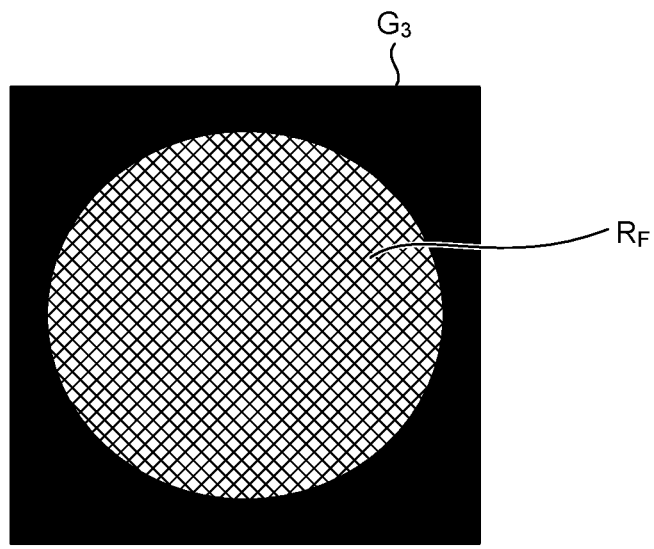
FIG. 16 is a diagram illustrating an example of a fluorescence image.

FIG. 16 is a diagram illustrating an example of a fluorescence image. In a fluorescence image $G_3$, a fluorescence image $R_F$ is visualized. At this point, for example, the irradiation range of the therapeutic light substantially coincides with the irradiation range of the guide light.

As illustrated in FIGS. 14 and 15, the first irradiation range of the light emitted from the white light source 311 is larger than the second irradiation range of the light emitted from the guide light source 613, and the first irradiation range includes the entire second irradiation range. Note that the therapeutic light is also emitted to a range similar to that of the guide light, and a fluorescence image is visualized in the image (see FIG. 16).

In the second embodiment described above, for the treatment, like in the first embodiment, for acquiring a white light image, the guide light is emitted together with the white light, whereas, for acquiring a fluorescence image, the fluorescence image is generated on the basis of an optical image in which the white light and the guide light are turned off and the excitation light is cut by the optical filter 243a. According to the second embodiment, the observation of the target site can be continued even at the time of fluorescence observation. Furthermore, according to the second embodiment, one sheet of imaging element 244 is included, and the excitation light incident on the imaging element 244 is cut by the optical filter 243a, and thus it is possible to prevent an increase in the diameter as compared with a configuration using two sheets of imaging elements.

In addition, according to the second embodiment, by making the emission port of the white light and the guide light or the therapeutic light the same, a deviation in the irradiation position due to the irradiation angle and the like are suppressed, and the usability is improved since it is not necessary to use the treatment tool 62.

Third Embodiment

Next, a third embodiment will be described. Since an endoscope system according to the third embodiment is the same as the endoscope system 1 according to the first embodiment, the description thereof will be omitted. In the third embodiment, the control related to dimming is different from that in the first embodiment. Hereinafter, dimming processing will be described. Note that the flow of treatment is similar to that of the first embodiment.

In a case where automatic dimming of the white light is performed using an image, if the light intensity of the guide light is high, the amount of the white light is adjusted so as to decrease depending on the magnitude of the signal value of the light intensity. If the amount of white light decreases, the entire image becomes dark. If the entire image is dark, a background image other than the guide light becomes unclear, and it may be difficult to distinguish the position of a tumor. Therefore, in the third embodiment, dimming control is performed so that the image does not become dark.

Figure 17:
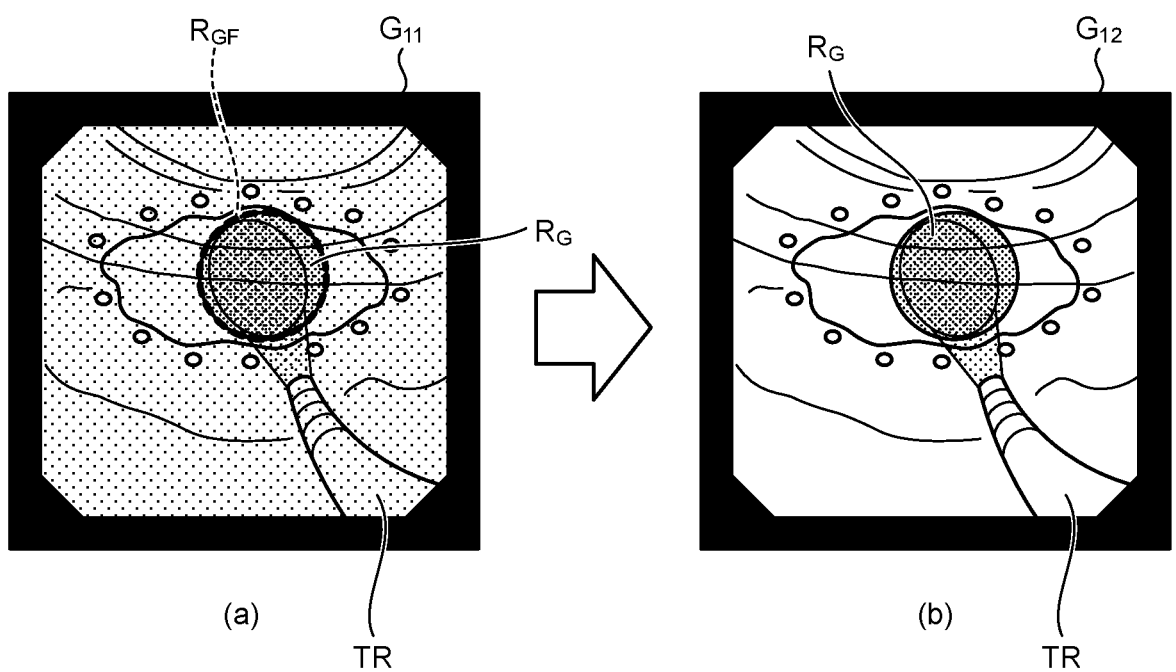
FIG. 17 is a diagram for explaining dimming processing of white light according to a third embodiment of the present invention.

FIG. 17 is a diagram for explaining the dimming processing according to the third embodiment of the present invention. (a) of FIG. 17 is a diagram illustrating a case where dimming control is performed including the signal value of the guide light. (b) of FIG. 17 is a diagram illustrating a case where the dimming control is performed excluding the influence of the guide light. At this point, the illumination controller 32 detects the irradiation range $R_G$ of the guide light in a white light image $G_{11}$ including an optical image of the guide light and sets a range including the irradiation range $R_G$ as a dimming exclusion region $R_{GF}$ (see (a) of FIG. 17). The illumination controller 32 calculates a signal value related to dimming of white light by using a signal value (for example, a luminance value) of a region excluding the set dimming exclusion region $R_{GF}$ or, by decreasing the signal value of the dimming exclusion region $R_{GF}$ on the basis of a preset condition, calculates a signal value related to dimming of white light by using a signal value of the entire image including the changed signal value. By generating the dimming signal by setting the dimming exclusion region $R_{GF}$ and adjusting the signal value of the region, a clear image in which a decrease in brightness of the white light image caused by the guide light is suppressed can be obtained (see (b) of FIG. 17).

In the third embodiment described above, for the treatment, like in the first embodiment, for acquiring a white light image, the guide light is emitted together with the white light, whereas, for acquiring a fluorescence image, the fluorescence image is generated on the basis of an optical image in which the white light and the guide light are turned off and the excitation light is cut by the optical filter 243a. According to the third embodiment, the observation of the target site can be continued even at the time of fluorescence observation. Furthermore, according to the third embodiment, one sheet of imaging element 244 is included, and the excitation light incident on the imaging element 244 is cut by the optical filter 243a, and thus it is possible to prevent an increase in the diameter as compared with a configuration using two sheets of imaging elements.

Furthermore, according to the third embodiment, by generating the dimming signal by setting the dimming exclusion region $R_{GF}$ and adjusting the handling of the signal value of the region, a decrease in the brightness of the image caused by the guide light is suppressed, and thus it is possible to suppress a decrease in the brightness of the white light image and to clarify the irradiation range of the guide light.

First Modification of Third Embodiment

Next, a first modification of the third embodiment will be described. Since an endoscope system according to the first modification is the same as the endoscope system 1 according to the first embodiment, the description thereof will be omitted. In the third embodiment, an example has been described in which the brightness of the white light image is controlled to clarify the irradiation range of the guide light on the premise of irradiation with the white light, however, in the first modification, the guide light is made clear by limiting the color components of light to be emitted and thereby illuminating.

Note that the flow of treatment using the endoscope system is similar to that of the first embodiment.

In the first modification, in a case where the guide light is emitted, the color components of the light emitted from the white light source is limited to the blue component and the green component or only the blue component, and light including the mentioned color component(s) is emitted as illumination light. By using the illumination light in which the color components are limited as the background of the image, it is possible to obtain an image in which the guide light is emphasized. At this point, at the time of outputting the image, the image in which green guide light is emphasized can be generated by using only blue and green signals.

Second Modification of Third Embodiment

Next, a second modification of the third embodiment will be described. An endoscope system according to the second modification is the same as the endoscope system 1 according to the first embodiment except that the treatment tool 62 is replaced with a treatment tool 62A, and thus description of the configuration other than the treatment tool 62A is omitted. In the third embodiment, the example has been described in which the brightness of the white light image is controlled to clarify the irradiation range of the guide light on the premise of irradiation with the white light, however, in the second modification, the guide light is emitted using a cylindrical-type fiber (cylindrical diffuser). Note that irradiation with the therapeutic light may also be performed using the cylindrical diffuser.

Note that the flow of treatment using the endoscope system is similar to that of the first embodiment.

Figure 18:
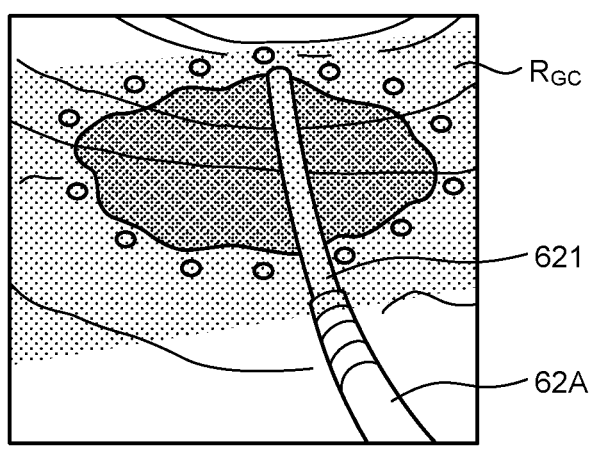
FIG. 18 is a diagram for explaining dimming processing according to a second modification of the third embodiment of the present invention.

FIG. 18 is a diagram for explaining dimming processing according to the second modification of the third embodiment of the present invention. In the present second modification, the treatment tool 62A includes a cylindrical diffuser 621 provided at an end portion opposite to a side connected to the treatment tool operating unit 61. The cylindrical diffuser 621 uniformly emits light in the circumferential direction of an optical fiber by a cylindrical emission chip. In the second modification, for example, light is uniformly emitted in the circumference with respect to the longitudinal direction of the cylindrical diffuser 621.

According to the second modification, since the guide light is emitted by the cylindrical diffuser 621, the guide light can be emitted over a wide range. Since the irradiation range of the guide light is wide, the structure around the treatment site can also be visualized by the guide light. At this point, since the illumination range is wide, the white light image generating unit 411 may generate a white light image (illumination light image) without emitting white light.

Fourth Embodiment

Next, a fourth embodiment will be described. Since an endoscope system according to the fourth embodiment is the same as the endoscope system 1 according to the first embodiment, the description thereof will be omitted. In the fourth embodiment, the treatment influence is corrected using an optical image of the guide light. Note that, in the fourth embodiment, description will be given on the premise that treatment is performed while a white light image is observed by emitting the white light and the guide light simultaneously with the therapeutic light.

Figure 19:
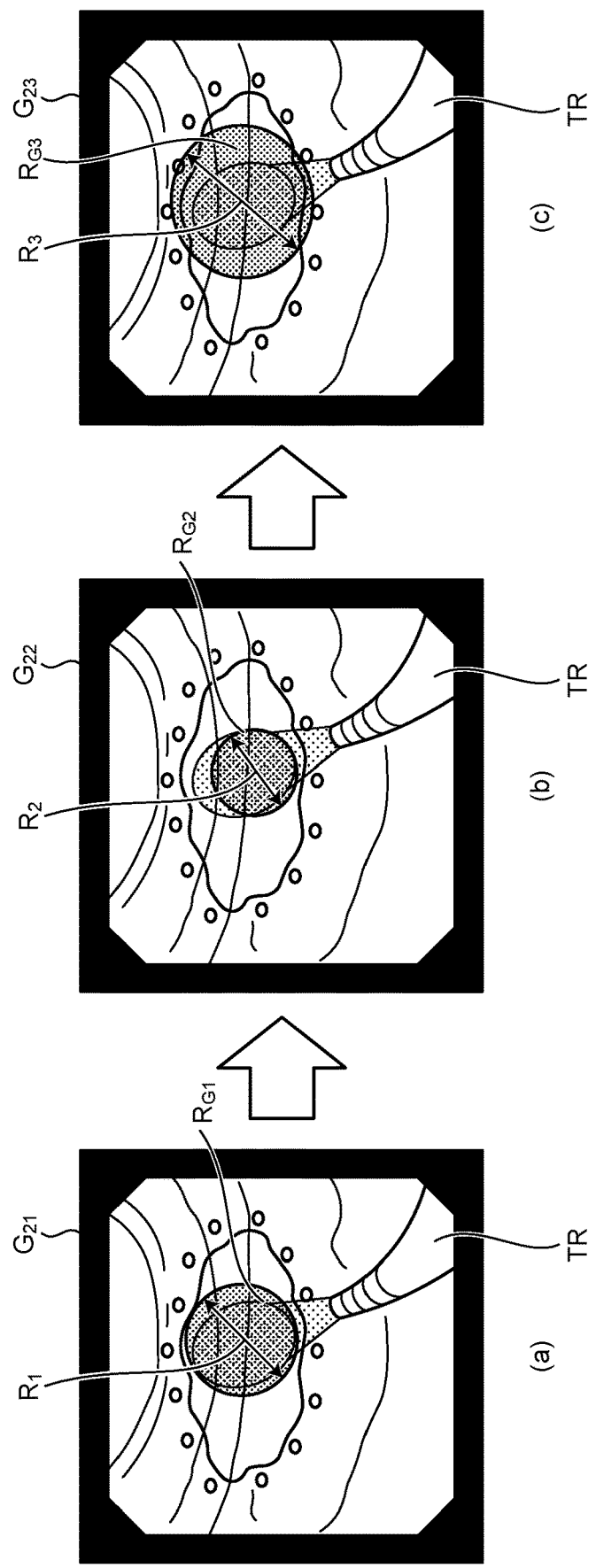
FIG. 19 is a diagram for explaining irradiation light amount correction of therapeutic light according to a fourth embodiment of the present invention.

FIG. 19 is a diagram for explaining irradiation light amount correction of therapeutic light according to the fourth embodiment of the present invention. The controller 44 measures the diameter $R_1$ (spot diameter) of an irradiation range $R_{G1}$ of the guide light captured in the white light image $G_{21}$ (see (a) of FIG. 19). For example, in a case where the amount of the therapeutic light necessary for the treatment is set to 100 J, the controller 44 calculates the treatment time by using the relationship between the size of a reference spot diameter set in advance and the amount of the therapeutic light. For example, the light amount is calculated to be 0.15 J from the diameter $R_1$ illustrated in (a) of FIG. 19, and the treatment time is calculated to be 667 seconds. The controller 44 causes the display 5 to display the calculated treatment time.

Thereafter, in a case where the position of the treatment tool 62 (treatment tool image TR) changes and the spot diameter changes, for example, in a case where the diameter $R_2$ of an irradiation range $R_{G2}$ of the guide light becomes smaller than the diameter $R_1$ as illustrated in (b) of FIG. 19, the light amount in the irradiation range increases. For example, in a case where the light amount is calculated to be 0.20 J from the diameter $R_2$, the cumulative light amount at the diameter $R_1$ is subtracted from 100 J, and a treatment time for reaching the remaining irradiation light amount is calculated.

Furthermore, in a case where the position of the treatment tool 62 changes and the spot diameter changes, for example, in a case where the diameter $R_3$ of the irradiation range $R_{G3}$ of the guide light becomes larger than the diameter $R_1$ as illustrated in (c) of FIG. 19, the light amount in the irradiation range decreases. For example, in a case where the light amount is calculated to be 0.10 J from the diameter $R_3$, the cumulative light amount at the diameter $R_1$ and the diameter $R_2$ is subtracted from 100 J, and a treatment time for reaching the remaining irradiation light amount is calculated.

In the fourth embodiment described above, like in the first embodiment, for acquiring a white light image, the guide light is emitted together with the white light, whereas, for acquiring a fluorescence image, the fluorescence image is generated on the basis of an optical image in which the white light and the guide light are turned off and the excitation light is cut by the optical filter 243a. According to the fourth embodiment, the observation of the target site can be continued even at the time of fluorescence observation. Furthermore, according to the fourth embodiment, one sheet of imaging element 244 is included, and the excitation light incident on the imaging element 244 is cut by the optical filter 243a, and thus it is possible to prevent an increase in the diameter as compared with a configuration using two sheets of imaging elements.

Furthermore, according to the fourth embodiment, by calculating and displaying the treatment time from the irradiation range of the guide light in the white light image, it is possible to reliably emit the light amount required for the treatment while suppressing excessive irradiation.

Note that, in the fourth embodiment, the example in which the treatment time is calculated from the irradiation range (irradiation diameter) of the guide light has been described, however, the treatment time may be calculated using the intensity (light intensity) of the guide light.

Furthermore, in the fourth embodiment, the example of calculating the treatment time on the basis of the optical image of the guide light has been described, however, the control may be performed by fixing the treatment time and calculating the intensity (light amount) of the guide light.

Fifth Embodiment

Next, a fifth embodiment will be described. Since an endoscope system according to the fifth embodiment is the same as the endoscope system 1 according to the first embodiment, the description thereof will be omitted. In the fifth embodiment, acquisition timing of a fluorescence image is controlled using signal values of the white light and the guide light.

The controller 44 monitors signal values of the white light and the guide light and irradiates the therapeutic light or captures a fluorescence image after both of the signal values decrease to predetermined values. Specifically, the controller 44 monitors the signal value of the guide light by detecting (a) signal value(s) of the blue component and/or the green component in an irradiation area of the guide light. Furthermore, the controller 44 monitors the signal value of the white light by detecting a signal value in an area other than the irradiation area of the guide light.

Figure 20:
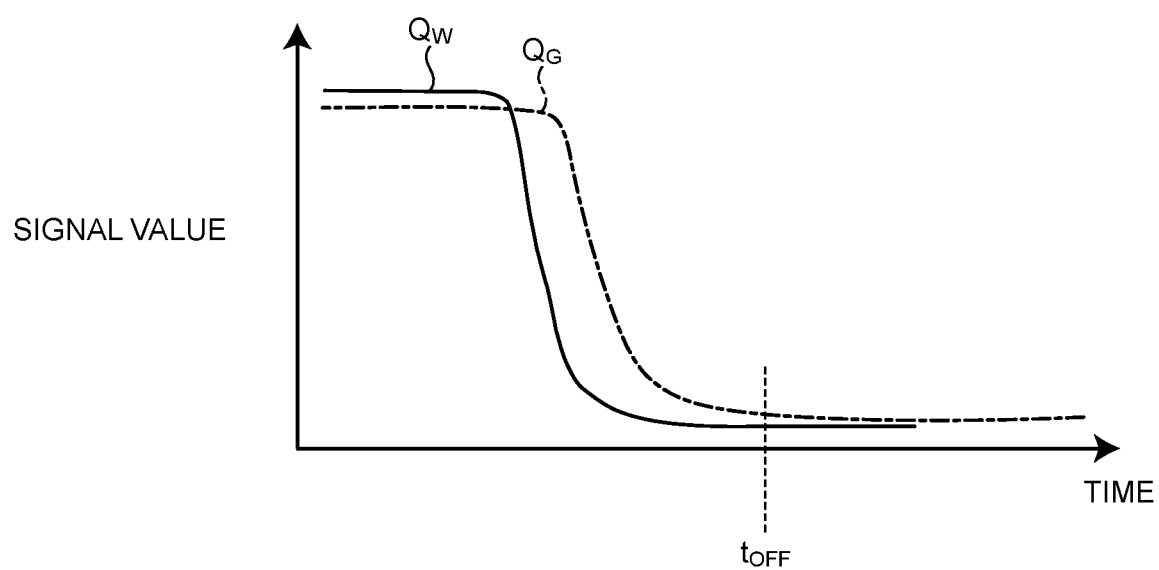
FIG. 20 is a diagram for describing fluorescence image acquiring timing according to a fifth embodiment of the present invention.

FIG. 20 is a diagram for describing fluorescence image acquiring timing according to the fifth embodiment of the present invention. In FIG. 20, a curve $Q_W$ indicates a signal value of the white light, and a curve $Q_C$ indicates a signal value of the guide light. The white light and the guide light are provided in different devices, and even when synchronized with each other, the timing of turning off the white light and the guide light may be shifted. The controller 44 monitors the signal values after the respective light sources are turned off and executes acquisition processing of a fluorescence image at time tor at which both of the signal values decrease to predetermined values. Note that the predetermined values set to the respective values may be the same or different from each other.

In the fifth embodiment described above, like in the first embodiment, for acquiring a white light image, the guide light is emitted together with the white light, whereas, for acquiring a fluorescence image, the fluorescence image is generated on the basis of an optical image in which the white light and the guide light are turned off and the excitation light is cut by the optical filter 243a. According to the fifth embodiment, the observation of the target site can be continued even at the time of fluorescence observation. Furthermore, according to the fifth embodiment, one sheet of imaging element 244 is included, and the excitation light incident on the imaging element 244 is cut by the optical filter 243a, and thus it is possible to prevent an increase in the diameter as compared with a configuration using two sheets of imaging elements.

Furthermore, according to the fifth embodiment, by controlling the acquisition timing of the fluorescence image on the basis of the signal values of the white light and the guide light, it is possible to acquire the fluorescence image in which the mixture of the white light and the guide light is suppressed.

Note that, in the embodiments and the modifications described above, the antibody drug used for PIT has been described as an example of the antibody drug, however, application is also possible to drugs used for other optical therapies such as photodynamic therapy (PDT).

Furthermore, in the above-described embodiments and modifications, the example in which the light source device 3 is separate from the processing device 4 has been described, however, the light source device 3 and the processing device 4 may be integrated. In addition, in the embodiments and the modifications, the example in which the treatment tool emits the therapeutic light has been described, however, the light source device 3 may emit the therapeutic light.

Note that, in the embodiments and the modifications described above, the description has been given on the premise that an endoscope system according to the present invention is the endoscope system 1 using the endoscope 2 that is flexible and observation target of which is a biological tissue or the like in a subject; however, applications are also possible to an endoscope system using a rigid endoscope or an endoscope in which a camera head is connected to an eyepiece of an optical endoscope such as an industrial endoscope, a fiberscope, or an optical tube for observing characteristics of a material.

INDUSTRIAL APPLICABILITY

As described above, an endoscope system according to the present invention is useful for continuously observing a treatment site at the time of fluorescence observation while preventing an increase in the diameter.

EXPLANATIONS OF LETTERS OR NUMERALS 1, 1A ENDOSCOPE SYSTEM
2 ENDOSCOPE
3 LIGHT SOURCE DEVICE
4 PROCESSING DEVICE
5 DISPLAY
6, 6A TREATMENT DEVICE
21 INSERTION UNIT
22 OPERATING UNIT
23 UNIVERSAL CORD
24 DISTAL END PORTION
25 BENDING UNIT
26 FLEXIBLE TUBE UNIT
31 LIGHT SOURCE UNIT
32 ILLUMINATION CONTROLLER
33 LIGHT SOURCE DRIVER
41 IMAGE PROCESSOR
42 SYNCHRONIZATION SIGNAL GENERATING UNIT
43 INPUT UNIT
44 CONTROLLER
45 STORAGE UNIT
61 TREATMENT TOOL OPERATING UNIT
62A TREATMENT TOOL
311 WHITE LIGHT SOURCE
411 WHITE LIGHT IMAGE GENERATING UNIT
412 FLUORESCENCE IMAGE GENERATING UNIT
413 SUPERIMPOSED IMAGE GENERATING UNIT
611 OPERATION INPUT UNIT
612 THERAPEUTIC LIGHT SOURCE
613 GUIDE LIGHT SOURCE
614 TREATMENT TOOL CONTROLLER

The invention claimed is:
1. An endoscope system comprising:
a controller configured to:
control an illumination light source to emit illumination light;
control a therapeutic light source to emit therapeutic light for causing a photoreactive reagent accumulated in a treatment target site to react;
control a guide light source to emit guide light having a wavelength shorter than a wavelength band of the therapeutic light;

control an imager to capture an optical image, the imager being arranged relative to an optical filter configured to cut light in the wavelength band of the therapeutic light and transmit a part of white light, the guide light, and fluorescence emitted by the photoreactive reagent to the imager;

control ON and OFF of the illumination light source and the guide light source and imaging timing of the imager in continuous synchronization with each other;

control ON and OFF of the therapeutic light source independently of the illumination light source and the guide light source; and cause an image processor to:
generate an illumination light image based on the optical image acquired during a period in which the illumination light source and the guide light source are controlled to be ON in synchronization; and generate a fluorescence image based on a fluorescence optical image acquired during a period in which the therapeutic light source is ON and the illumination light source and the guide light source are controlled to be OFF in synchronization.

2. The endoscope system according to claim 1, wherein the image processor is configured to generate the illumination light image based on the optical image by emission of the illumination light and the guide light and a superimposed image in which the fluorescence image based on the optical image by the fluorescence is superimposed on the illumination light image, and the endoscope system further includes:
a display configured to display the illumination light image and/or the superimposed image.

3. The endoscope system according to claim 1, wherein the controller is configured to control ON and OFF of the illumination light source and the guide light source, ON and OFF of the therapeutic light source, and imaging timing of the imager in synchronization with each other.

4. The endoscope system according to claim 1, wherein the illumination light source is subjected to dimming control using a value obtained by subtracting a signal value corresponding to an amount of the guide light which is emitted, from a detected light amount.

5. The endoscope system according to claim 1, wherein the illumination light source is subjected to dimming control based on a light amount in a range excluding an irradiation range of the guide light.

6. The endoscope system according to claim 1, wherein the illumination light source is configured to emit the illumination light in a first wavelength band other than a second wavelength band of the guide light.

7. The endoscope system according to claim 1, wherein the illumination light source is configured to emit light of only both of a blue component and a green component or only the blue component.

8. The endoscope system according to claim 1, wherein the controller is configured to cause the image processor to generate the illumination light image based on the optical image acquired during the period in which the illumination light source and the guide light source are ON and the therapeutic light source is OFF.

9. The endoscope system according to claim 1, wherein the controller is configured to cause the imager to capture the fluorescence image when a signal value of at least one of a blue component and a green component in the optical image acquired during a period in which the illumination light source and the guide light source are OFF is less than or equal to a preset threshold value.

10. The endoscope system according to claim 1, wherein the controller is configured to normalize the fluorescence image by using a light intensity or an irradiation range of an irradiation area of the guide light in the illumination light image.

11. The endoscope system according to claim 1, wherein the controller is configured to correct an amount of the therapeutic light by using a light intensity or an irradiation range of an irradiation area of the guide light in the illumination light image.

12. The endoscope system according to claim 1, wherein the controller is configured to correct a light intensity of the therapeutic light with a distance using a light intensity or an irradiation range of the guide light and calculate a treatment time using the light intensity that has been corrected.

13. A method performed by a controller of an endoscope system, the method comprising:

controlling an illumination light source to emit illumination light;

controlling a therapeutic light source to emit therapeutic light for causing a photoreactive reagent accumulated in a treatment target site to react;

controlling a guide light source to emit guide light having a wavelength shorter than a wavelength band of the therapeutic light;

controlling an imager to capture an optical image, the imager being arranged relative to an optical filter configured to cut light in the wavelength band of the therapeutic light and transmit a part of white light, the guide light, and fluorescence emitted by the photoreactive reagent to the imager;

controlling ON and OFF of the illumination light source and the guide light source and imaging timing of the imager in continuous synchronization with each other;

controlling ON and OFF of the therapeutic light source independently of the illumination light source and the guide light source; and causing an image processor to:
generate an illumination light image based on the optical image acquired during a period in which the illumination light source and the guide light source are controlled to be ON in synchronization; and generate a fluorescence image based on a fluorescence optical image acquired during a period in which the therapeutic light source is ON and the illumination light source and the guide light source are controlled to be OFF in synchronization.

14. The method according to claim 13 further comprising generating the illumination light image based on the optical image by emission of the illumination light and the guide light and a superimposed image in which the fluorescence image based on the optical image by the fluorescence is superimposed on the illumination light image, and controlling a display of the endoscope system to display the illumination light image and/or the superimposed image.

15. The method according to claim 13, further comprising:
controlling ON and OFF of the illumination light source and the guide light source, ON and OFF of the therapeutic light source, and imaging timing of the imager in synchronization with each other.

16. The method according to claim 13, further comprising:
causing the image processor to:
generate the illumination light image based on the optical image acquired during the period in which the illumination light source and the guide light source are ON and the therapeutic light source is OFF.

17. A non-transitory computer-readable medium that stores a computer-executable program including instructions that, when executed by a computer of an endoscope system, cause the computer to:
control an illumination light source to emit illumination light;
control a therapeutic light source to emit therapeutic light for causing a photoreactive reagent accumulated in a treatment target site to react;
control a guide light source to emit guide light having a wavelength shorter than a wavelength band of the therapeutic light;
control an imager to capture an optical image, the imager being arranged relative to an optical filter configured to cut light in the wavelength band of the therapeutic light and transmit a part of white light, the guide light, and fluorescence emitted by the photoreactive reagent to the imager;
control ON and OFF of the illumination light source and the guide light source and imaging timing of the imager in continuous synchronization with each other;
control ON and OFF of the therapeutic light source independently of the illumination light source and the guide light source; and
cause an image processor to:
generate an illumination light image based on the optical image acquired during a period in which the illumination light source and the guide light source are controlled to be ON in synchronization; and
generate a fluorescence image based on a fluorescence optical image acquired during a period in which the therapeutic light source is ON and the illumination light source and the guide light source are controlled to be OFF in synchronization.

18. The non-transitory computer-readable medium according to claim 17, wherein the instructions, when executed by the computer, cause the computer to:
generate the illumination light image based on the optical image by emission of the illumination light and the guide light and a superimposed image in which the fluorescence image based on the optical image by the fluorescence is superimposed on the illumination light image, and
control a display of the endoscope system to display the illumination light image and/or the superimposed image.

19. The non-transitory computer-readable medium according to claim 17, wherein the instructions, when executed by the computer, cause the computer to:
control ON and OFF of the illumination light source and the guide light source, ON and OFF of the therapeutic light source, and imaging timing of the imager in synchronization with each other.

20. The non-transitory computer-readable medium according to claim 17,
wherein the instructions, when executed by the computer, cause the computer to:
cause the image processor to:
generate the illumination light image based on the optical image acquired during the period in which the illumination light source and the guide light source are ON and the therapeutic light source is OFF.

* * * * *